(12) United States Patent
Ananthan

(10) Patent No.: US 9,163,030 B2
(45) Date of Patent: Oct. 20, 2015

(54) HETEROCYCLE-FUSED MORPHINANS, USE THEREOF AND PREPARATION THEREOF

(71) Applicant: Southern Research Institute, Birmingham, AL (US)

(72) Inventor: Subramaniam Ananthan, Birmingham, AL (US)

(73) Assignee: Southern Research Institute, Birmingham, AL (US)

( * ) Notice: Subject to any disclaimer, the term of this patent is extended or adjusted under 35 U.S.C. 154(b) by 0 days.

(21) Appl. No.: 14/398,588

(22) PCT Filed: May 2, 2013

(86) PCT No.: PCT/US2013/039242
§ 371 (c)(1),
(2) Date: Nov. 3, 2014

(87) PCT Pub. No.: WO2013/166271
PCT Pub. Date: Nov. 7, 2013

(65) Prior Publication Data
US 2015/0094324 A1    Apr. 2, 2015

Related U.S. Application Data

(60) Provisional application No. 61/641,355, filed on May 2, 2012.

(51) Int. Cl.
| A61K 31/485 | (2006.01) |
| C07D 489/08 | (2006.01) |
| C07D 491/18 | (2006.01) |
| C07D 489/02 | (2006.01) |
| C07D 489/06 | (2006.01) |

(52) U.S. Cl.
CPC ............ C07D 491/18 (2013.01); C07D 489/02 (2013.01); C07D 489/06 (2013.01); C07D 489/08 (2013.01)

(58) Field of Classification Search
USPC .......................................... 514/279; 546/40
See application file for complete search history.

(56) References Cited

U.S. PATENT DOCUMENTS

| 6,465,479 | B1 * | 10/2002 | Ananthan | 514/279 |
| 7,105,675 | B2 * | 9/2006 | Ananthan | 546/40 |
| 7,534,799 | B2 * | 5/2009 | Ananthan | 514/279 |
| 7,541,364 | B2 * | 6/2009 | Ananthan et al. | 514/279 |
| 7,951,817 | B2 | 5/2011 | Ananthan et al. | |
| 2008/0064712 | A1 | 3/2008 | Schmidhammer et al. | |

FOREIGN PATENT DOCUMENTS

WO    WO-9602545 A1    2/1996

OTHER PUBLICATIONS

Ananthan, S. et al.: 14-alkoxy- and 14-acyloxypyridomorphinans: mu agonist/delta anatgonist opioid analgesics with diminished tolerance and dependence side effects. J. Medicinal Chemistry, vol. 55, pp. 8350-8363, 2012.*
Ananthan, S. et al.: Identification of opioid ligands possessing mixed mu agonist/ delta antagonist activity among pyridomorphinans derived from naloxone, oxymorphone, and hydromorphone. J. Med. Chem., vol. 47, pp. 1400-1412, 2004.*
Ananthan, S. et al.: Synthesis, opioid receptor binding, and biological activities of Naltrexone-derived pyrido- and pyrimidomorphinans. J. Med. Chem., vol. 42, pp. 3527-3538, 1999.*

* cited by examiner

Primary Examiner — Charanjit Aulakh
(74) Attorney, Agent, or Firm — Novak Druce Connolly Bove + Quigg LLP

(57) ABSTRACT

Provided are compounds of the formula:

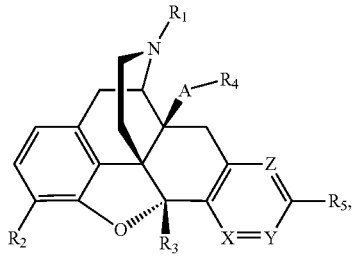

$R_1$; $R_2$, $R_3$; $R_4$; A; X; Y and Z are defined in the present disclosure; pharmaceutically acceptable salts thereof, deuterium forms thereof, isomers thereof, and mixture thereof; and processes for their preparation. The compounds can be used for treating a patient suffering from a condition that is capable of treatment with an agonist and/or antagonist of the opioid receptors and are especially useful a patient suffering from pain, treating a patient in need of an immunosuppressant to prevent rejection in organ transplant and skin graft, in need of an anti-allergic agent, in need of an anti-inflammatory agent, in need of a brain cell protectant, for drug and/or alcohol abuse, to decrease gastric secretion, for diarrhea, for cardiovascular disease, for a respiratory disease, in need of a cough and/or respiratory depressant, for mental illness, for epileptic seizures and other neurologic disorders.

16 Claims, 6 Drawing Sheets

HETEROCYCLE-FUSED MORPHINANS, USE THEREOF AND PREPARATION THEREOF

CROSS REFERENCE TO RELATED APPLICATIONS

This application is a National Phase filing under 35 U.S.C. §371 of PCT/US13/039242 filed on May 2, 2013; and this application claims the benefit of U.S. Provisional Application No. 61/641,355, filed on May 2, 2012. The entire content of each application is hereby incorporated by reference.

FEDERALLY SPONSORED RESEARCH AND DEVELOPMENT

This invention was supported by Grant DA 008883 from the National Institute on Drug Abuse of the National Institutes of Health and the US Government has certain rights in the invention.

TECHNICAL FIELD

The present disclosure relates to certain heterocycle fused morphianans. Compounds of the present disclosure are mixed mu agonist delta antagonists or dual mu agonist/delta agonists or antagonists at mu, delta and kappa opioid receptors. Compounds of the present disclosure are useful as analgesics and as treatment agents for neurological and other disorders where opioid systems play a modulatory or pathological role. More particularly compounds of the present disclosure are useful for treating a patient in need of an analgesic for pain relief, in need of an immunosuppressant to prevent rejection in organ transplant and skin graft, in need of an anti-allergic agent, in need of an anti-inflammatory agent, in need of a brain cell protectant, for drug and/or alcohol abuse, to decrease gastric secretion, for diarrhea, for cardiovascular disease, for a respiratory disease, in need of a cough and/or respiratory depressant, for mental illness, for epileptic seizures and other neurologic disorders.

BACKGROUND

Chronic pain represents a major health and economic problem throughout the world.

Despite major advances in understanding the physiological and pathological basis of pain, an ideal analgesic is yet to be discovered. Among analgesic drugs, the opioid class of compounds still remains the effective treatment agents for severe and chronic pain. For instance, see Parrot, Using opioid analgesic to manage chronic non-cancer pain in primary care, J. Am. Board Fam. Pract, 1999, 12, 293-306 and Cherny, New strategies in opioid therapy for cancer pain, J. Oncol. Manage 2000, 9, 8-15.

The existence of three opioid receptor types, mu opioid receptors (MOR), delta opioid receptor (DOR) and kappa opioid receptor (KOR) has been clearly established and is confirmed by cloning of these three receptors from mouse, rat, and human cDNAs. Along these lines, see Dhawan et al., International Union of Pharmacology. XII. Classification of Opioid Receptors, Pharmacol. Rev. 1996, 48, 567-592; and McCurdy et al., *Opioid Receptor Ligands. In Burger's Medicinal Chemistry, Drug Discovery and Development,* 7th ed.; Abraham et al., Eds. John Wiley & Sons: New York, N.Y., 2010.

All three opioid receptor types are located in the human central nervous system and each has a role in the mediation of pain. Morphine and related opioids currently prescribed as potent analgesics for the treatment of pain produce their analgesic activity primarily through their agonist action at the mu opioid receptors. The general administration of these medications is limited by significant side effects such as respiratory depression, muscle rigidity, emesis, constipation, tolerance, and physical dependence. For example, see Duthie, Adverse Effects of Opioid Analgesic Drugs, Br. J. Anaesth. 1987, 59, 6177 and van Ree et al., Opioids, Reward and Addiction: An Encounter of Biology, Psychology, and Medicine. Pharmacol. Rev. 1999, 51, 341-396.

A large body of evidence indicates the existence of physiological and functional interactions between mu and delta receptors. Ligands with agonist or antagonist action at the delta receptor, for example, have been shown to modulate the analgesic and adverse effects of mu agonists. See, for instance, Traynor et al., Delta opioid receptor subtypes and cross-talk with mu receptors. Trends Pharmacol. Sci. 1993, 14, 84-86; Rothman et al., Allosteric Coupling Among Opioid Receptors: Evidence for an Opioid Receptor Complex, In Handbook of Experimental Pharmacology, Volume 104, Opioid I; Hertz et al., Eds; Springer-Verlag; Berlin, 1993; pp. 217-237; Jordan et al., G-Protein-coupled receptor heterodimerization modulates receptor function. Nature 1999, 399, 697-700; George et al., Oligomerization of mu and delta Opioid Receptors, J. Biol. Chem. 2000, 275, 26128-26135; Levac et al., Oligomerization of opioid Receptors: Generation of novel signaling units, Curr. Opin. Pharmacol., 2002, 2, 76-81.

On the other hand, agonist action at the delta receptors potentiate mu receptor mediated analgesic effects and antagonist action at the delta receptor suppresses the tolerance, physical dependence, and related side effects off mu agonists without affecting their analgesic activity. In a study using the nonpeptide ligand naltrindole, Abdelhamid et al. demonstrated that the delta receptor antagonist greatly reduced the development of morphine tolerance and dependence in mice in both the acute and chronic models without affecting the analgesic actions of morphine. See Abdelhamid et al., Selective blockage of delta opioid receptors prevents the development of morphine tolerance and dependence in mice. J. Pharmacol. Exp. Ther. 1991, 258, 299-303. Fundytus et al., reported that continuous infusion of the delta selective antagonist TIPP[Ψ] by the intracerbroventricular (icv) route in parallel with continuous administration of morphine by the subcutaneous route to rats attenuated the development of morphine tolerance and dependence to a large extent. See Fundytus, et al., Attenuation of morphine tolerance and dependence with the highly selective delta-opioid receptor antagonist TIPP[Ψ]. Eur. J. Pharmacol 1995, 286, 105-108.

Schiller et al., found that the peptide ligand DIPP-NH2[Ψ] displayed mixed mu agonist/delta antagonist properties in vitro and that the compound given icv produced analgesic effect with no physical dependence and less tolerance than morphine in rats. See Schiller et al., Four different types of Opioid Peptides with mixed mu agonist/delta Antagonist Properties Analgesia 1995, 1, 703-706; and Schiller et al., The Opioid mu agonist/delta antagonist DIPP-NH2-[Ψ] produces a potent analgesic effect, no physical dependence, and less tolerance than morphine in rats, J. Med. Chem. 1999, 42, 3520-3526.

Studies with antisense oligonucleotides of delta receptors have demonstrated that reduction of receptor expression diminishes the development and/or expression of morphine dependence without compromising antinociception produced by mu agonists. See Suzuki et al., Antisense oligodeoxynucleotide to delta opioid receptors attenuates morphine dependence in mice, Life Sci. 1997, 61, PL 165-170; and Sanchez-Blazquez et al., Antisense oligodeoxynucleotides to opioid mu and delta receptors reduced morphine dependence in mice: Role of delta-2 opioid receptors, J. Pharmacsol. Exp. Ther. 1997, 280, 1423-1431. Furthermore, genetic deletion studies using delta receptor knockout mice have shown that these mutant mice retain supraspinal analgesia and do not develop analgesic tolerance to morphine. Zhu et al., Retention of supraspinal delta-like analgesia and loss of morphine tolerance in delta opioid receptor knockout mice, Neuron, 1999, 24, 243-252.

Discovery of nonpeptide opioid ligands possessing a balanced profile of mixed mu agonist/delta antagonist activity has been a challenge. In an early study focusing on naltrexone-derived heterocycle annulated morphinan ligands, it was found that compounds arising by fusion of a heteroaromatic ring such as a pyridine ring on the C5-C6 of the C-ring gave pyridomorphinans that displayed high affinity binding at the opioid receptors. The binding affinity and functional activity are modulated by the substituents placed at the 5'-position on the pyridine moiety. For example, the introduction of aromatic groups such as a phenyl group or a 1-pyrrolyl group at this position gave ligands with high binding affinity and improved antagonist potency as determined in bioassays using mouse vas deferens smooth muscle preparations. See Ananthan et al., Synthesis, opioid receptor binding, and biological activities of naltrexone-derived pyrido- and pyrimidomorphinans, J. Med. Chem. 1999, 42, 3527-3538; and Ananthan et al., Synthesis, opioid receptor binding, and functional activity of 5'-substituted 17-cyclopropylmethylpyrido[2',3':6,7]morphinans. Bioorg. Med. Chem. Lett. 2003, 13, 529-532.

Interestingly, among phenyl ring substituted analogues, the p-chlorophenyl compound displayed a mixed mu agonist/delta antagonist profile of activity in the smooth muscle assays in vitro. In analgesic activity evaluations, this compound displayed partial agonist activity in the tail-flick assay and a full agonist activity in the acetic acid writhing assay after icv or ip administration in mice, and it did not produce tolerance to antinociceptive effects on repeated ip injections. Studies in mice with selective antagonists, characterized this compound as a partial mu agonist/delta antagonist. See Wells et al., In Vivo Pharmacological Characterization of SoRI 9409, a Nonpeptidic opioid mu-agonist/delta-antagonist that produces limited antinociceptive tolerance and attenuates morphine physical dependence. J. Pharmacol. Exp. Ther. 2001, 297, 597-605. In in vitro biochemical assays using [$^{35}$S]GTP-γ-S binding, this compound, however, failed to display mu agonist activity in guinea pig caudate membranes as well as in cloned cells expressing human mu receptors. See Xu et al., SoRI-9409, a Non-peptide opioid mu receptor agonist/delta receptor antagonist, fails to stimulate [$^{35}$S]-GTP-γ-S binding at cloned opioid receptors. brain res. bull. 2001, 55, 507-511. A similar pyridine annulations strategy when applied to oxymorphone and hydromorphone frameworks led to ligands that displayed mixed mu agonist/delta antagonist activity although with somewhat weak mu agonist potency. See Ananthan et al., Identification of ligands possessing mixed μ agonist/δ antagonist activity among pyridomorphinans derived from naloxone, oxymorphone, and hydromorphone. J. Med. Chem. 2004, 47, 1400-1412.

Bivalent ligands possessing a mu agonist unit such as oxymorphone tethered to a delta antagonist unit such as naltrindole by a 16 to 21 atom chain have been investigated as ligands targeting mu-delta heterodimers. Among such compounds, bivalent ligand whose spacer was 16 atoms or longer produced less dependence than morphine; ligands possessing spacer lengths of 19 atoms or greater produced less physical dependence and tolerance. See Daniels et al., Opioid-induced tolerance and dependence in mice is modulated by the distance between pharmacophores in a bivalent ligand series. Proc. Natl. Acad. Sci. U.S.A. 2005, 102, 19208-19213.

Schmidhammer and coworkers explored a number of morphinans possessing an alkoxy substituent at the 14-position. The morphinan templates explored include 6-oxomorphinans, 6-aminomorphinans, indolomorphinans and benzofuromorphinans. Depending upon the template and the substituents, compounds with varying profiles were obtained. See Schmidhammer, et al., Synthesis and biological evaluation of 14-alkoxymorphinans. 4. Opioid agonists and partial opioid agonists in a series of N-(cyclobutylmethyl)-14-methoxymorphinan-6-ones. Helv. Chim. Acta 1989, 72, 1233-1240; Schmidhammer et al., Synthesis and biological evaluation of 14-alkoxymorphinans. 1. Highly potent opioid agonists in the series of (−)-14-methoxy-N-methylmorphinan-6-ones. J. Med. Chem. 1984, 27, 1575-1579; Schmidhammer et al. Synthesis and biological evaluation of 14-alkoxymorphinans. (−)-N-(cyclopropylmethyl)-4,14-dimethoxymorphinan-6-one, a selective mu opioid receptor antagonist. J. Med. Chem. 1989, 32, 418-421; Schmidhammer et al., *Opioid Receptor Antagonists*. Elsevier: New York, 1998; pp. 83-132; Schmidhammer, et al., 14-Alkoxymorphinans-A series of highly potent opioid agonists, antagonists, and partial agonists. Curr. Top. Med. Chem. 1993, 1, 261-276. Some of the compounds especially those derived from 6-oxomorphinans with 3-phenylpropoxy group at the 14-position were very potent nonselective opioid agonists with no measurable antagonist activity. See Greiner et al., Synthesis and biological evaluation of 14-alkoxymorphinans. 18. N-substituted 14-phenylpropyloxymorphinan-6-ones with unanticipated agonist properties: extending the scope of common structure-activity relationships. J. Med. Chem. 2003, 46, 1758-1763; Lattanzi et al. Synthesis and biological evaluation of 14-alkoxymorphinans. 22. (1) Influence of the 14-alkoxy group and the substitution in position 5 in 14-alkoxymorphinan-6-ones on in vitro and in vivo activities. J. Med. Chem. 2005, 48, 3372-3378.

There have been suggestions that antagonists at MOR, DOR and KOR are potentially useful as immunosuppressants, anti-allergic and anti-inflammatory agents and as treatment agents for addiction, drug abuse, alcoholism, obesity and a variety of neurological diseases. See Schmidhammer et al., *Opioid Receptor Antagonists*. Elsevier: New York, 1998; pp. 83-132.

SUMMARY OF DISCLOSURE

The present disclosure relates to the discovery compounds that display (a) mixed MOR agonist/DOR antagonist, (b) dual MOR/DOR agonists or (c) MOR/DOR/KOR antagonist activities. Compounds of the present disclosure are represented by following formula (I)

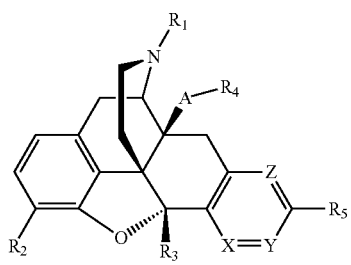

wherein $R_1$ is selected from the group consisting of H, linear or branched $C_{1-6}$ alkyl, $C_{3-7}$ cycloalkyl, cycloalkylalkyl having 3-7 carbon atoms in the cycloalkyl ring, each of the latter three groups being optionally substituted by a hydroxyl group when C≥2, $C_{3-5}$ alkenyl, aryl, arylalkyl, heterocycloalkyl or $(CH_2)_nCOR$, wherein n is 0 to 5 and R represents a linear or branched $C_{1-6}$ alkyl, hydroxyl, $C_{1-5}$ alkoxy, $OC_{3-6}$ alkenyl or arylalkyl or heterocycloalkyl, $NR_6R_7$ where $R_6$ and $R_7$ may be the same or different, and each is H, linear or branched $C_{1-6}$ alkyl, cycloalkylalkyl having 3-7 carbon atoms in the cycloalkyl ring, $C_{3-5}$ alkenyl, aryl, heterocyclo, arylalkyl or heterocycloalkyl; or $R_1$ is a group D-E wherein D represents $C_{1-10}$ alkylene and E represents substituted or unsubstituted aryl or heterocyclo;

$R_2$ is selected from the group consisting of H, linear or branched $C_{1-6}$ alkyl, hydroxyl, $C_{1-5}$ alkoxy, halogen, and $(CH_2)_nCOR$, where n and R have the same meanings as described above, $SR_6$, nitro, $NR_6R_7$, $NHCOR_6$, $NHSO_2R_6$, $R_6$ and $R_7$ have the same meanings as described above, $R_3$ is hydrogen or $C_{1-6}$ alkyl;

$R_4$ is selected from the group consisting of H, linear or branched $C_{1-6}$ alkyl, cycloalkylalkyl having 3-7 carbon atoms in the cycloalkyl ring, $C_{3-5}$ alkenyl, aryl, heterocyclo, arylalkyl, and heterocycloalkyl; or $R_4$ is a group D-E wherein D represents $C_{1-10}$ alkylene and E represents substituted or unsubstituted aryl or heterocyclo; or $COR_6$;

A is selected from the group consisting of O, S, $NR_6$ and $CH_2$;

X is N;

Y is selected from the group consisting of N, $CR_6$ and $CCOR_6$;

Z is selected from the group consisting of N, $CR_6$ and $CCOR_6$; and $R_5$ is selected from the group consisting of $R_6$ and $COR_6$;

pharmaceutically acceptable salts thereof, deuterated forms thereof, isomers thereof, solvates thereof, and mixtures thereof.

Another aspect of the present disclosure relates to treating a patient suffering from a condition that is capable of treatment with an agonist and/or antagonist of the opioid receptors which comprising administering to said patient an effective amount of at least one of the above disclosed compounds, pharmaceutically acceptable salts thereof, deuterated forms thereof, isomers thereof, solvates thereof, or mixture thereof.

A still further aspect of the present disclosure relates to treating a patient suffering from pain which comprises administering to the patient a pain treating effective amount of at least one of the above disclosed compounds, pharmaceutically acceptable salts thereof, deuterated forms thereof, isomers thereof, solvates thereof, or mixture thereof.

Other aspects of the present disclosure are concerned with treating a patient in need of an immunosuppressant to prevent rejection in organ transplant and skin graft, in need of an anti-allergic agent, in need of an anti-inflammatory agent, in need of a brain cell protectant, for drug and/or alcohol abuse, to decrease gastric secretion, for diarrhea, for cardiovascular disease, for a respiratory disease, in need of a cough and/or respiratory depressant, for mental illness, for epileptic seizures and other neurologic disorders which comprising administering to said patient an effective amount of at least one of the above disclosed compounds, pharmaceutically acceptable salts thereof, deuterated forms thereof, isomers thereof, solvates thereof, or mixture thereof.

The present disclosure is also concerned with a process for the preparation of the above disclosed compounds, pharmaceutically acceptable salts thereof, deuterated forms thereof, isomers thereof, solvates thereof, or mixtures thereof which comprises subjecting a 17-substituted-3,14-dihydroxypyridomorphinan to dialkylation at the phenolic hydroxyl at the 3-position and the tertiary alcohol at the 14-position followed by selective dealkylation of the phenolic ether function.

Still other objects and advantages of the present disclosure will become readily apparent by those skilled in the art from the following detailed description, wherein it is shown and described only the preferred embodiments, simply by way of illustration of the best mode. As will be realized, the disclosure is capable of other and different embodiments, and its several details are capable of modifications in various obvious respects, without departing from the disclosure. Accordingly, the description is to be regarded as illustrative in nature and not as restrictive.

BEST AND VARIOUS MODES FOR CARRYING OUT DISCLOSURE

Figure 1:
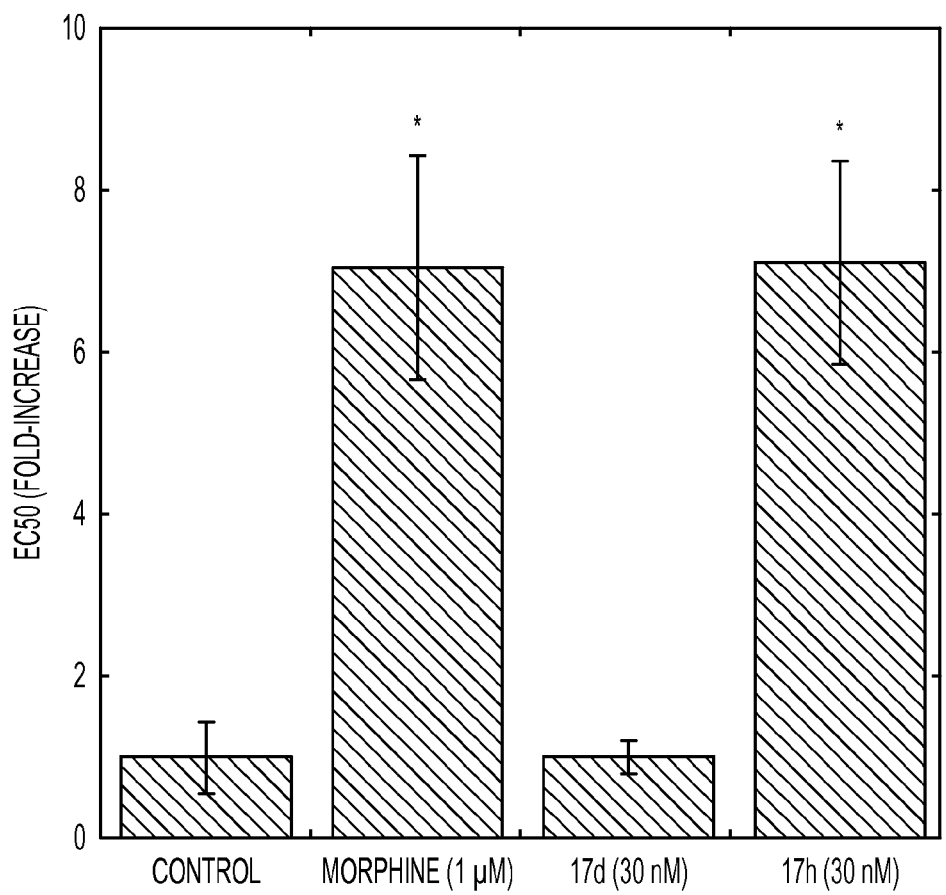
FIG. 1 is a graph comparing the effects of chronic drug treatment on DAMGO-mediated inhibition of forskolin-stimulated cAMP accumulation in MOR/DOR dimer cells with various compounds including compounds of the present disclosure.

Compounds of the present disclosure are represented by following formula (I).

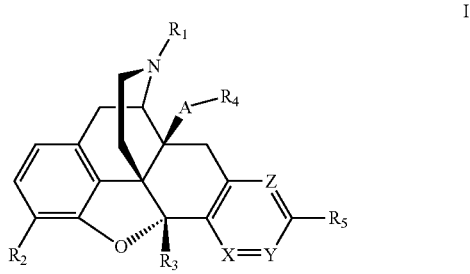

wherein $R_1$ is selected from the group consisting of H, linear or branched $C_{1-6}$ alkyl, $C_{3-7}$ cycloalkyl, cycloalkylalkyl having 3-7 carbon atoms in the cycloalkyl ring, each of the latter three groups being optionally substituted by a hydroxyl group when C≥2, $C_{3-5}$ alkenyl, aryl, arylalkyl, heterocycloalkyl or $(CH_2)_nCOR$, wherein n is 0 to 5 and R represents a linear or branched $C_{1-6}$ alkyl, hydroxyl, $C_{1-5}$ alkoxy, $OC_{3-6}$ alkenyl or arylalkyl or heterocycloalkyl, $NR_6R_7$ where $R_6$ and $R_7$ may be the same or different, and each is H, linear or branched $C_{1-6}$ alkyl, cycloalkylalkyl having 3-7 carbon atoms in the cycloalkyl ring, $C_{3-5}$ alkenyl, aryl, heterocyclo, arylalkyl or heterocycloalkyl; or $R_1$ is a group D-E wherein D represents $C_{1-10}$ alkylene and E represents substituted or unsubstituted aryl or heterocyclo;

$R_2$ is selected from the group consisting of H, linear or branched $C_{1-6}$ alkyl, hydroxyl, $C_{1-5}$ alkoxy, halogen, and $(CH_2)_nCOR$, where n and R have the same meanings as described above, $SR_6$, nitro, $NR_6R_7$, $NHCOR_6$, $NHSO_2R_6$, $R_6$ and $R_7$ have the same meanings as described above, $R_3$ is hydrogen or $C_{1-6}$ alkyl;

$R_4$ is selected from the group consisting of H, linear or branched $C_{1-6}$ alkyl, cycloalkylalkyl having 3-7 carbon atoms in the cycloalkyl ring, $C_{3-5}$ alkenyl, aryl, heterocyclo, arylalkyl, and heterocycloalkyl; or $R_4$ is a group D-E wherein D represents $C_{1-10}$ alkylene and E represents substituted or unsubstituted aryl or heterocyclo; or $COR_6$;

A is selected from the group consisting of O, S, $NR_6$ and $CH_2$;

X is N;

Y is selected from the group consisting of N, $CR_6$ and $CCOR_6$;

Z is selected from the group consisting of N, $CR_6$ and $CCOR_6$; and $R_5$ is selected from the group consisting of $R_6$ and $COR_6$;

pharmaceutically acceptable salts thereof, deuterated forms thereof, isomers thereof, solvates thereof, and mixtures thereof.

Listed below are definitions of various terms used to describe this invention. These definitions apply to the terms as they are used throughout this specification, unless otherwise limited in specific instances, either individually or as part of a larger group.

The term "aryl" refers to monocyclic or bicyclic aromatic hydrocarbon groups having 6 to 12 carbon atoms in the ring portion, such as phenyl, naphthyl, biphenyl, and diphenyl groups, each of which may be substituted. Some typical substitutions for the aryl group include amino, nitro, halo and alkyl.

The term "alkyl" refers to straight or branched chain unsubstituted hydrocarbon groups of 1 to 20 carbon atoms, more typically 1 to 6 carbon atoms and even more typically 1 to 4 carbon atoms.

Examples of suitable alkyl groups include methyl, ethyl and propyl. Examples of branched alkyl groups include isopropyl and t-butyl.

The alkoxy group typically contains 1 to 6 carbon atoms. Suitable alkoxy groups typically contain 1-6 carbon atoms and include methoxy, ethoxy, propoxy and butoxy.

The term "alkenyl" refers to straight or branched chain unsubstituted hydrocarbon groups typically having 3 to 6 carbon atoms.

The term "aralkyl" or alkylaryl refers to an aryl group bonded directly through an alkyl group, such as benzyl or phenethyl.

The term "cycloalkyl" refers cyclic hydrocarbon ring systems typically containing 3-9 carbon atoms, with typical examples being cyclopropyl, cyclobutyl, cyclopentyl, cyclohexyl, and cycloheptyl.

The term "cycloalkylalkyl" refers to alkyl substituted cyclic hydrocarbon ring system wherein the cyclic hydrocarbon typically contains 3-7 carbon atoms, a typical example being cyclopropylalkyl.

The term "heterocyclo", refers to an optionally substituted, saturated or unsaturated aromatic or nonaromatic cyclic group, for example, which is a 4 to 7 membered monocyclic, 7 to 11 membered bicyclic, or 10 to 15 membered tricyclic ring system, which has at least one heteroatom and at least one carbon atom in the ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized.

Examples of N-heterocyclo groups are pyridyl, pyrrolidinyl, piperidinyl, piperazinyl, pyridinyl, pyrrolyl, pyrazolyl, pyrazinyl pyrimidinyl, pyridazinyl, imidazoyl and imidazolidinyl, 1,2,3 triazole and 1,2,4 triazole. Examples of O-heterocyclic groups are furanyl and pyranyl. Examples of S-heterocyclic groups are thiopyran and thiophene. Examples of heterocyclic groups containing both N and O are morpholinyl, oxazole, and isooxazole. Example of heterocyclic groups containing both N and S are thiomorpholine, thiazole and isothiazole.

Examples of halo groups are Cl, F, Br and I. An example of a haloalkyl group is trifluoromethyl.

"Pharmaceutically acceptable salts" refer to derivatives of the disclosed compounds wherein the parent compound is modified by making acid or base salts thereof. The compounds of this disclosure form acid addition salts with a wide variety of organic and inorganic acids and includes the physiologically acceptable salts which are often used in pharmaceutical chemistry. Such salts are also part of this disclosure. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkonic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromobenzenesulfonate, chlorobenzenesulfonate, ethanesulfonate, 2-hydroxyethanesulfonate, methanesulfonate, naphthalene-1-sulfonate, naphthalene-2-sulfonate, p-toleunesulfonate, xylenesulfonate, tartarate, and the like.

The deuterated forms contain heavy hydrogen including deuterium and/or tritium.

It is understood that the compounds of the present disclosure relate to all optical isomers and stereo-isomers at the various possible atoms of the molecule, unless specified otherwise.

"Solvates" refers to the compound formed by the interaction of a solvent and a solute and includes hydrates. Solvates are usually crystalline solid adducts containing solvent molecules within the crystal structure, in either stoichiometric or nonstoichiometric proportions.

Prodrug forms of the compounds bearing various nitrogen functions (amino, hydroxyamino, amide, etc.) may include the following types of derivatives where each R group individually may be hydrogen, substituted or unsubstituted alkyl, aryl, alkenyl, alkynyl, heterocycle, alkylaryl, aralkyl, aralkenyl, aralkynyl, cycloalkyl or cycloalkenyl groups as defined earlier.

(a) Carboxamides, —NHC(O)R
(b) Carbamates, —NHC(O)OR
(c) (Acyloxy)alkyl Carbamates, NHC(O)OROC(O)R
(d) Enamines, —NHCR(=CHCO2R) or —NHCR(=CHCONR2)
(e) Schiff Bases, —N=CR2

A group of preferred compounds of the formula (I) is that in which $R_1$ is $C_{1-6}$ alkyl, cycloalkylalkyl having 4-6 carbon atoms in the cycloalkyl ring or arylalkyl and $R_2$ is hydroxyl or methoxy, $R_3$ is hydrogen or methyl, A is O, NH or $CH_2$, and $R_4$ is $C_{1-6}$ alkyl, $C_{3-5}$ alkenyl, 3-aryl-2-propenyl or 3-heteroaryl-2-propenyl, and X, Y, Z and $R_5$ are as defined above.

Particularly preferred compounds of the formula (I) are those in which A is O and $R_5$ is substituted or unsubstituted aryl or heteroaryl.

Some specific compounds according to the present invention are the following:

5'-(4-Chlorophenyl)-17-(cyclopropylmethyl)-6,7-didehydro-4,5α-epoxy-3-hydroxy-14-methoxypyrido[2',3':6,7]morphinan (17a).

14-(Benzyloxy)-5'-(4-chlorophenyl)-17-(cyclopropylmethyl)-6,7-didehydro-4,5α-epoxy-3-hydroxypyrido[2',3':6,7]morphinan (17b).

5'-(4-Chlorophenyl)-14-cinnamyloxy-17-(cyclopropylmethyl)-6,7-didehydro-4,5α-epoxy-3-hydroxypyrido[2',3':6,7]morphinan (17c).

5'-(4-Chlorophenyl)-17-(cyclopropylmethyl)-6,7-didehydro-4,5α-epoxy-3-hydroxy-14-(3-phenylpropoxy)pyrido[2',3':6,7]morphinan (17d).

5'-(4-Chlorophenyl)-6,7-didehydro-4,5α-epoxy-3-hydroxy-14-methoxy-17-methylpyrido[2',3':6,7]morphinan (17e).

14-Benzyloxy-5'-(4-chlorophenyl)-6,7-didehydro-4,5α-epoxy-3-hydroxy-17-methylpyrido[2',3':6,7]morphinan (17f).

5'-(4-Chlorophenyl)-14-cinnamyloxy-6,7-didehydro-4,5α-epoxy-3-hydroxy-17-methylpyrido[2',3':6,7]morphinan (17g).

5'-(4-Chlorophenyl)-6,7-didehydro-4,5α-epoxy-3-hydroxy-17-methyl-14-(3-phenylpropoxy)pyrido[2',3':6,7]morphinan (17h).

14-Benzoyloxy-5'-(4-chlorophenyl)-17-(cyclopropylmethyl)-6,7-didehydro-4,5α-epoxy-3-hydroxypyrido[2',3':6,7]morphinan (18a).

5'-(4-Chlorophenyl)-17-(cyclopropylmethyl)-6,7-didehydro-4,5α-epoxy-3-hydroxy-14-(3-phenylacetoxy)pyrido[2',3':6,7]morphinan (18b).

5'-(4-Chlorophenyl)-17-(cyclopropylmethyl)-6,7-didehydro-4,5α-epoxy-3-hydroxy-14-(3-phenylpropionyloxy)pyrido[2',3':6,7]morphinan (18c).

14-Benzoyloxy-5'-(4-chlorophenyl)-6,7-didehydro-4,5α-epoxy-3-hydroxy-17-methylpyrido[2',3':6,7]morphinan (18d).

5'-(4-Chlorophenyl)-6,7-didehydro-4,5α-epoxy-3-hydroxy-17-methyl-14-(phenylacetoxy)pyrido[2',3':6,7]morphinan (18e).

5'-(4-Chlorophenyl)-6,7-didehydro-4,5α-epoxy-3-hydroxy-17-methyl-14-(3-phenylpropionyloxy)pyrido[2',3':6,7]morphinan (18f).

3,14-Dibenzoyloxy-5'-(4-chlorophenyl)-17-(cyclopropylmethyl)-6,7-didehydro-4,5α-epoxy-3-hydroxypyrido[2',3':6,7]morphinan (21).

3-Benzoyloxy-5'-(4-chlorophenyl)-17-(cyclopropylmethyl)-6,7,8,14-tetradehydro-4,5α-epoxypyrido[2',3':6,7]morphinan (22).

5'-(4-Chlorophenyl)-17-(cyclopropylmethyl)-3-hydroxy-6,7,8,14-tetradehydro-4,5α-epoxypyrido[2',3':6,7]morphinan (23).

Compounds of the present disclosure can be prepared from commercially available morphinan ketones using the pyridine annulation methodology described earlier followed by appropriate functional group transformation methods as shown in Scheme 1 and Scheme 2.

For the synthesis of the desired target compounds, the previously reported 17-cyclopropylmethyl- and 17-methyl-3,14-dihydroxypyridomorphinans 6 (Ananthan et al., Synthesis, opioid receptor binding, and biological activities of naltrexone-derived pyrido- and pyrimidomorphinans. J. Med. Chem. 1999, 42, 3527-3538) and 9 (Ananthan et al., Identification of opiod ligands possessing mixed μ agonist/δ antagonist activity among pyridomorphinans derived from naloxone, oxymorphonem and hydromorphone. J. Med. Chem. 2004, 47, 1400-1412) served as suitable starting materials. For the synthesis of 14-alkoxy target compounds we found it convenient to perform dialkylation at the phenolic hydroxyl at the 3-position and the tertiary alcohol at the 14-position followed by selective dealkylation of the phenolic ether function. Thus, dimethylation of 6 with dimethyl sulfate or dialkylation of 6 or 9 with appropriate alkyl bromides using sodium hydride as the base yielded the corresponding dialkyl derivatives 19a-d and 19f. Treatment of these with boron tribromide led to selective removal of the alkyl group from the ether function at C-3 yielding the target compounds 17a-d and 17f. For the preparation of 17e, 17g and 17h, the oxycodone-derived pyridomorphinan 20 (Ananthan et al., Identification of opiod ligands possessing mixed μ agonist/δ antagonist activity among pyridomorphinans derived from naloxone, oxymorphone and hydromorphone. J. Med. Chem. 2004, 47, 1400-1412) was used as the starting material. Alkylation of 20 with the appropriate alkylating agent followed by 3-O-demethylation of the resulting diethers 19e, 19g and 19h delivered the desired target compounds (Scheme 1).

Scheme 1. Synthesis of 14-Alkoxypyridomorphinans 17a-h$^a$

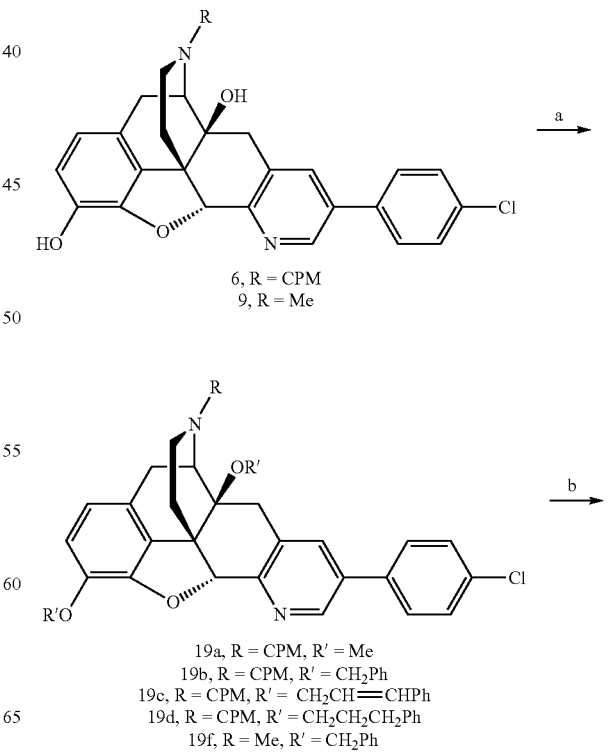

6, R = CPM
9, R = Me

19a, R = CPM, R' = Me
19b, R = CPM, R' = CH$_2$Ph
19c, R = CPM, R' = CH$_2$CH=CHPh
19d, R = CPM, R' = CH$_2$CH$_2$CH$_2$Ph
19f, R = Me, R' = CH$_2$Ph

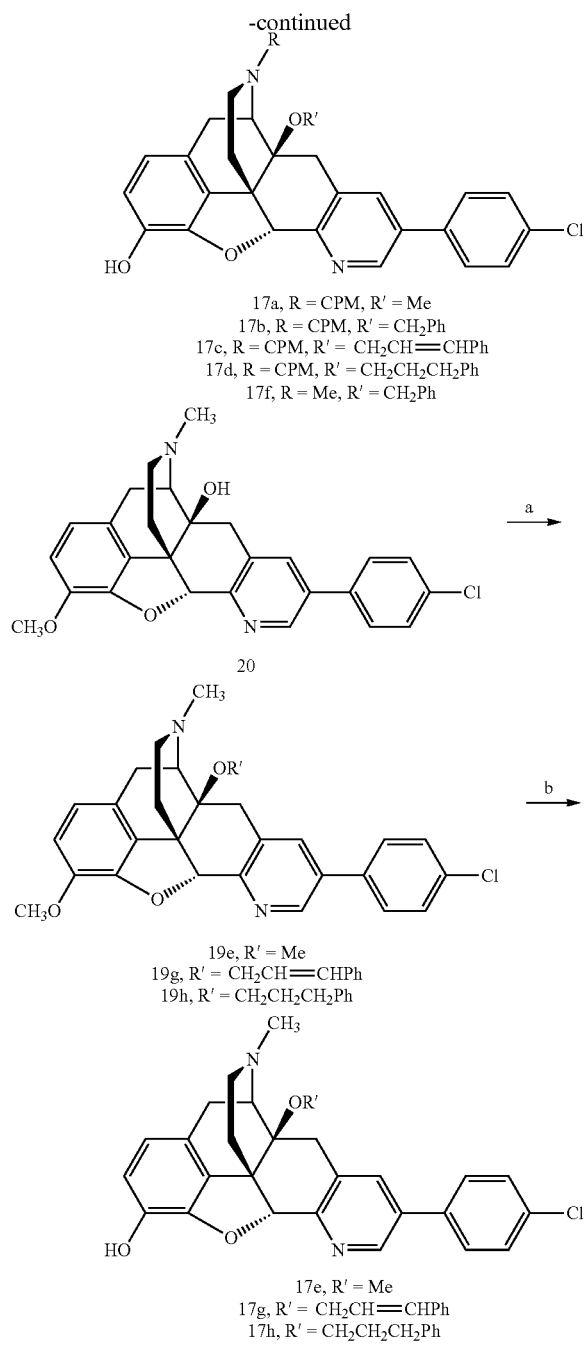

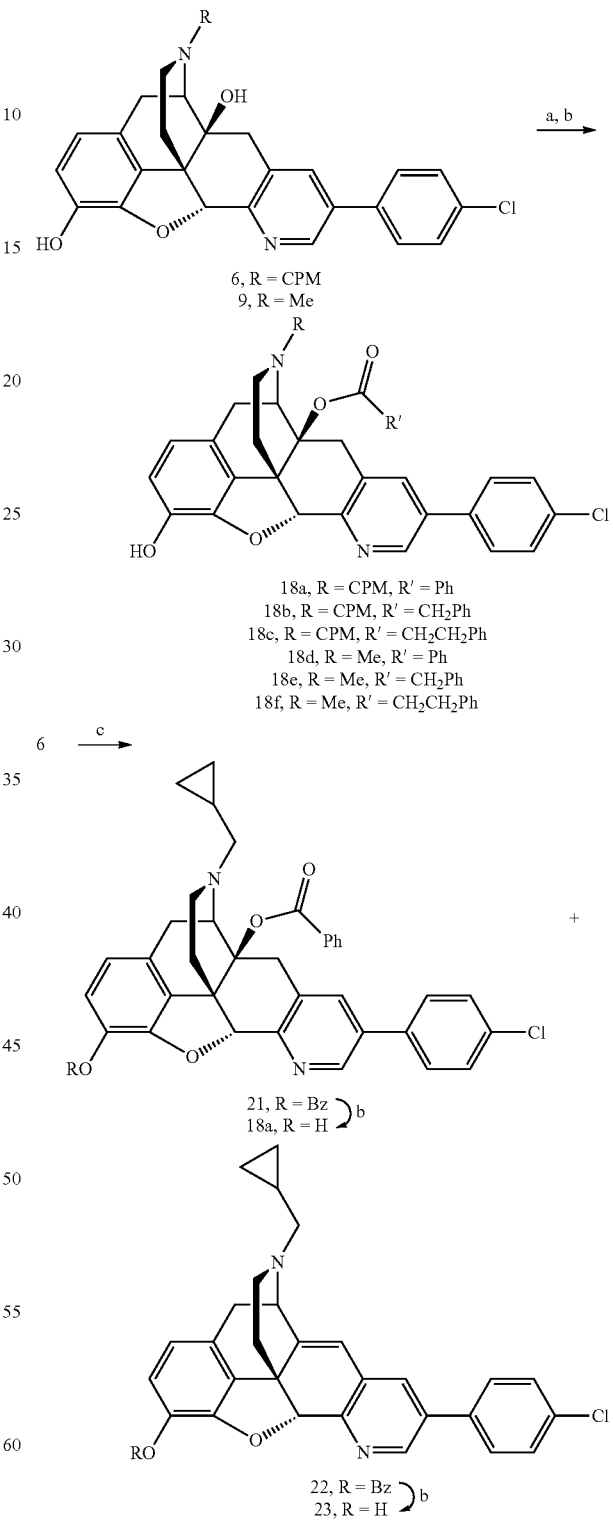

Scheme 2. Synthesis of 14-Acyloxypyridomorphinans 18a-f and 21-23[a]

[a]Reagents and conditions: (a) R'COCl, Et₃N, DMF or PhMe; (b) K₂CO₃, MeOH—H₂O, rt; (c) PhCOCl, Et₃N, DMF and 22 could be converted to the free phenolic compounds 18a and 23, respectively, by treatment with $K_2CO_3$ in aqueous methanol (Scheme 2).

The starting materials 6 and 9 were reacted with an excess of the appropriate acid chloride and the resulting intermediates were treated with aqueous base to remove the acyl group from the phenolic hydroxyl group to obtain the desired 14-O-acylated target compounds 18a-f. The yields of the final products in these acylation reactions were only modest possibly due to elimination reactions setting in as side reactions. For example, isolation of the products from the reaction of 6 with benzoyl chloride after a 5 h reaction time gave the dibenzoate 21 and the elimination product 22 in 60:40 ratio. When the reaction was allowed to proceed for a longer period of time (16 h) the elimination product became the main product with a distribution ratio of 26:74 for 21 and 22. These benzoates 21

The following non-limiting Examples are presented to further illustrate the present disclosure. The melting points were determined in open capillary tubes with a Mel-Temp melting point apparatus and are uncorrected. $^1$H NMR spectra were recorded on a Nicolet 300NB spectrometer operating at 300.635 MHz. Chemical shifts are expressed in parts per million downfield from tetramethylsilane. Spectral assignments were supported by proton decoupling. Mass spectra were recorded on a Varian MAT 311A double-focusing mass spectrometer in the fast atom bombardment (FAB) mode or on a Bruker BIOTOF II in electrospray ionization (ESI) mode. Analytical results indicated by elemental symbols were within ±0.4% of the theoretical values. Thin layer chromatography (TLC) was performed on Analtech silica gel GF 0.25 mm plates. Flash column chromatography was performed with E. Merck silica gel 60 (230-400 mesh). Yields are of purified compounds and were not optimized. On the basis of NMR and combustion analysis, all final compounds were >95% pure.

Example 1

5'-(4-Chlorophenyl)-17-(cyclopropylmethyl)-6,7-didehydro-4,5α-epoxy-3-hydroxy-14-methoxypyrido[2',3':6,7]morphinan (17a)

Step 1.

Sodium hydride (0.096 g, 4.0 mmol, 60% dispersion in mineral oil, washed with hexanes) was added to a stirred solution of 6 (0.487 g, 1.0 mmol) in DMF (7 mL) at 0-5° C. The mixture was stirred at 0° C. for 10 min, treated dropwise with dimethyl sulfate (0.277 g, 2.2 mmol) and then allowed to warm to room temperature. The mixture was stirred at room temperature overnight and then was quenched by addition of small pieces of ice. The mixture was diluted with water (20 mL) and extracted with $CHCl_3$ (2×25 mL). The combined extracts were washed with water and brine, dried over anhydrous sodium sulfate, filtered, and concentrated under reduced pressure to yield 0.3 g (58%) of 5'-(4-chlorophenyl)-17-(cyclopropylmethyl)-6,7-didehydro-3,14-dimethoxy-4,5α-epoxypyrido[2',3':6,7]morphinan (19a). ESI MS m/z 515 $(MH)^+$. The crude product thus obtained was used in the next step without further purification.

Step 2.

A solution of 19a (0.26 g, 0.5 mmol) in anhydrous $CH_2Cl_2$ (7 mL) was cooled to −78° C. and treated dropwise with boron tribromide (0.75 g, 3.0 mmol). The mixture was stirred at −78° C. for 1 h and then allowed to come to room temperature. After quenching the reaction by addition of drops of ice-cold water, the mixture was extracted with $CHCl_3$ (2×50 mL), dried over anhydrous sodium sulfate, filtered, and concentrated under reduced pressure. The crude product was purified over silica gel column using $CHCl_3$-MeOH—$NH_4OH$ (98:1.5:0.5) to yield 0.18 g (72%) of desired product 17a.

MP 170-173° C.; TLC $R_f$ 0.39 ($CHCl_3$-MeOH, 95:5); $^1$H NMR (DMSO-$d_6$) δ 0.12-0.54 (2 m, 4H, cyclopropyl $CH_2CH_2$), 0.84-0.88 (m, 1H, cyclopropyl CH), 1.43-1.47 (m, 1H, C-15H), 2.16-2.68 (m, 7H, C-15H, C-8H, C-10H, C-16$H_2$, NCH$_2$), 3.01 (d, 1H, J=17.2 Hz, C-8H), 3.11 (m, 1H, C-10H), 3.17 (s, 31H, OCH$_3$), 3.6 (m, 1H, C-9H), 5.32 (s, 1H, C-5H), 6.52 (s, 2H, C-2H, C-1H), 7.53-7.56 (m, 2H, C-3"H, C-5"H), 7.71-7.77 (m, 3H, C-4'H, C-2"H, C-6"H), 8.76 (s, 1H, C-6'H), 9.04 (s, 1H, C-3 OH). ESI MS m/z 501 $(MH)^+$. Anal. ($C_{30}H_{29}ClN_2O_3.H_2O$) C, H, N.

Example 2

14-(Benzyloxy)-5'-(4-chlorophenyl)-17-(cyclopropylmethyl)-6,7-didehydro-4,5α-epoxy-3-hydroxypyrido[2',3':6,7]morphinan (17b)

Step 1.

A solution of 6 (0.487 g, 1.0 mmol) in DMF (5.0 mL) was reacted with sodium hydride (0.12 g, 3.0 mmol, 60% dispersion in mineral oil, washed with hexane) and benzyl bromide (0.35 g, 2.2 mmol) as described in Step 1 for the preparation of 17a. Purification of the crude product by chromatography over a column of silica using $CHCl_3$-MeOH, 99:1 yielded 0.46 g (69%) of 3,14-bis(benzyloxy)-5'-(4-chlorophenyl)-17-(cyclopropylmethyl)-6,7-didehydro-4,5α-epoxypyrido[2',3':6,7]morphinan (19b). ESI MS m/z 667 $(MH)^+$.

Step 2.

A solution of 19b (0.46 g, 0.7 mmol) in anhydrous $CH_2Cl_2$ (5.0 mL) was cooled to −78° C. and treated dropwise with boron tribromide (3.0 mL of 1 M solution in $CH_2Cl_2$, 3.0 mmol). The mixture was stirred at −78° C. for 1 h and then allowed to attain to room temperature. The reaction was quenched by the addition of water (10 mL). The mixture was extracted with $CHCl_3$ (2×50 mL), dried with anhydrous sodium sulfate, filtered, and the solvent was removed under reduced pressure. The residue was purified over the column of silica gel using EtOAc-hexane (1:1) as the eluent. The product obtained was crystallized from EtOAc to afford 0.098 g (25%) of 17b.

MP 130-132° C.; TLC $R_f$ 0.42 ($CHCl_3$-MeOH, 95:5); $^1$H NMR (DMSO-$d_6$) δ 0.08-0.19 and 0.44-0.54 (m, 4H, cyclopropyl $CH_2CH_2$), 0.84-0.96 (m, 1H, cyclopropyl CH), 1.50 (d, 1H, J=10.6 Hz, C-15H), 2.20-2.28 (m, 1H, C-15H), 2.34-2.82 (m, 7H, C-16 $H_2$, C-10H, C-8$H_2$), NCH$_2$-cyclopropyl), 3.10-3.23 (m, 1H, C-10H), 3.82 (d, 1H, J=5.7 Hz, C-9H), 4.35 (dd, 2H, J=11.1 and 11.4 Hz, OCH$_2$), 5.38 (s, 1H, C-5H), 6.52-6.57 (m, 2H, C-1H, C-2H), 7.10-7.45 (5H, $C_6H_5$), 7.53-7.56 (m, 2H, C-3"H, C-5"H), 7.70-7.74 (m, 3H, C-4'H, C-2"H, C-6"H), 8.79 (d, 1H, J=2.2 Hz, C-6'H), 8.96 (s, 1H, C-3 OH). ESI MS m/z 577 $(MH)^+$. Anal. ($C_{36}H_{33}ClN_2O_3.H_2O$) C, H, N.

Example 3

5'-(4-Chlorophenyl)-14-cinnamyloxy-17-(cyclopropylmethyl)-6,7-didehydro-4,5α-epoxy-3-hydroxypyrido[2',3':6,7]morphinan (17c)

Step 1.

To a stirred solution of 6 (0.974 g, 2.0 mmol) in DMF (15 mL) was added sodium hydride (60% dispersion in mineral oil, 0.288 g, 6.0 mmol) at 0-5 DC. After stirring at 0° C. for 10 minutes, cinnamyl bromide (0.871 g, 4.4 mmol) was added dropwise. The mixture was stirred at room temperature overnight, and the reaction was quenched by careful addition of small pieces of ice. The mixture was diluted with water and extracted with $CHCl_3$ (2×50 mL). The combined organic extracts were washed with water, brine and dried over anhydrous sodium sulfate. The crude product obtained after removal of the solvent under reduced pressure was purified over a column of silica using EtOAc-hexane 20:80 to yield 0.524 g (36%) of 5'-(4-chlorophenyl)-17-(cyclopropylmethyl)-3,14-(dicinnamyloxy)-6,7-didehydro-4,5α-epoxypyrido[2',3':6,7]morphinan (19c). ESI MS m/z 719 $(MH)^+$. The product thus obtained was used in the next step without further purification.

Step 2.

A solution of 19c (0.524 g, 0.73 mmol) in anhydrous $CH_2Cl_2$ (7 mL) was cooled to −78° C. Boron tribromide (1.08 g, 6.0 mmol) was added dropwise. After stirring for 1 h, the reaction mixture was allowed to attain room temperature. The reaction mixture was quenched by addition of drops of ice-cold water. After dilution with water, the crude product was extracted with $CHCl_3$ (2×100 mL), dried over anhydrous sodium sulfate, filtered and evaporated under reduced pressure. The crude product was purified by column chromatography over silica using EtOAc-hexane 25:75 as the eluent to obtain 0.268 g (61%) of 17c.

MP 138-140° C.; TLC R$_f$ 0.35 (CHCl$_3$-MeOH, 95:5); $^1$H NMR (DMSO-d$_6$) δ0.06-0.23 (m, 2H, cyclopropyl CH$_2$), 0.43-0.57 (2m, 2H, cyclopropyl CH$_2$), 0.83-0.99 (m, 1H, cyclopropyl CH), 1.43-1.53 (m, 1H, C-15H), 2.12-2.76 (m, 7H, C-16H$_2$, C-8H, C-10H, NCH$_2$-cyclopropyl, C-15H), 2.99 (m, 2H, C-8H, C-10H), 3.70 (d, 1H, J=5.61 Hz, C-9H), 4.05-4.39 (m, 2H, OCH$_2$), 5.41 (s, 1H, C-5H), 6.05-6.35 (m, 2H, CH=CH), 6.50 (s, 2H, C-2H, C-1H), 6.88-7.18 (m, 5H, C$_6$H$_5$), 7.45-7.78 (m, 5H, C-5"H, C-3"H, C-4'H, C-2"H, C-6"H), 8.8 (d, 1H, J=2.2 Hz, C-6'H), 9.06 (s, 1H, C-3 OH). ESI MS m/z 603 (MH)$^+$. Anal. (C$_{38}$H$_{35}$ClN$_2$O$_3$.0.5H$_2$O) C, H, N.

Example 4

5'-(4-Chlorophenyl)-17-(cyclopropylmethyl)-6,7-didehydro-4,5α-epoxy-3-hydroxy-14-(3-phenylpropoxy)pyrido[2',3':6,7]morphinan (17d)

Step 1.

To a stirred solution of 6 (1.948 g, 4.0 mmol) in DMF (40 mL) was added sodium hydride (0.96 g, 24 mmol, 60% dispersion in mineral oil, washed with hexanes) at 0-5° C. After allowing the mixture to stir for 10 minutes, 3-phenylpropyl bromide (1.752 g, 8.8 mmol) was added dropwise. The reaction mixture was allowed to come to room temperature and stirred for 2 days. Excess of sodium hydride was decomposed with drops of ice-cold water, the mixture was then diluted with water and extracted with CHCl$_3$ (2×100 mL). The organic extracts were washed with water and brine, dried over anhydrous sodium sulfate, and the solvent was removed under reduced pressure. The residue was purified by chromatography over a column of silica gel using EtOAc-hexane 20:80 as the eluent to obtain 5'-(4-Chlorophenyl)-17-(cyclopropylmethyl)-6,7-didehydro-4,5α-epoxy-3,14-bis(3-phenylpropoxy)pyrido[2',3':6,7]morphinan (19d). Yield 0.96 g (34%). ESI MS m/z 723 (MH)$^+$.

Step 2.

A solution of 19d (0.92 g, 1.27 mmol) in anhydrous CH$_2$Cl$_2$ (25 mL) was cooled to −78° C. Boron tribromide (3.18 g, 12.7 mmol) was added dropwise and the mixture was stirred for 1 h. The mixture was then allowed to come to room temperature and the reaction was quenched by addition of drops of ice-cold water. The mixture was diluted with water and extracted with CHCl$_3$. The organic layer was dried over anhydrous sodium sulfate, concentrated under reduced pressure and the residue was purified by chromatography over a column of silica using EtOAc-hexane 1:1 to obtain 0.23 g (28%) of the desired product (17d)

MP118-120° C.; TLC R$_f$ 0.36 (CHCl$_3$-MeOH, 95:5); $^1$H NMR (DMSO-d$_6$) δ0.06-0.23 (m, 2H, cyclopropyl CH$_2$), 0.43-0.57 (2m, 2H, cyclopropyl CH$_2$), 0.83-0.99 (m, 1H, cyclopropyl CH), 1.43-1.53 (m, 1H, C-15H), 2.12-2.76 (m, 7H, C-16H$_2$, C-8H, C-10H, NCH$_2$, C-15H), 2.99 (m, 2H, C-8H, C-10H), 3.70 (d, 1H, J=5.61 Hz, C-9H), 4.05-4.39 (m, 2H, OCH$_2$), 5.41 (s, 1H, C-5H), 6.05-6.35 (m, 4H, CH$_2$CH$_2$), 6.50 (s, 2H, C-2H, C-1H), 6.88-7.18 (m, 5H, C$_6$H$_5$), 7.45-7.78 (m, 5H, C-5"H, C-3"H, C-4'H, C-2"H, C-6"H), 8.80 (d, 1H, J=2.2 Hz, C-6'H), 9.06 (s, 1H, C-3 OH). ESI MS m/z 605 (MH)$^+$. Anal. (C$_{38}$H$_{37}$ClN$_2$O$_3$) C, H, N.

Example 5

5'-(4-Chlorophenyl)-6,7-didehydro-4,5α-epoxy-3-hydroxy-14-methoxy-17-methylpyrido[2',3':6,7]morphinan (17e)

Step 1.

A stirred solution of 20 (0.69 g, 1.5 mmol) in DMF (15 mL) was cooled to 0-5° C. and sodium hydride (0.21 g, 45.25 mmol, 60% dispersion in mineral oil, washed with hexanes) was added. The mixture was stirred at 0° C. for 10 minutes and then treated dropwise with dimethyl sulfate (0.277 g, 1.8 mmol). The mixture was stirred at room temperature overnight and excess sodium hydride was destroyed by addition of ice-cold water. The mixture was diluted with water and the product was extracted with CHCl$_3$ (2×25 mL). The organic extracts were washed with water and brine, dried over anhydrous sodium sulfate and concentrated under reduced pressure. The crude product was purified by over a column of silica using CHCl$_3$-MeOH—NH$_4$OH 97:2.5:0.5 as the eluent to obtain 0.29 g (41%) of the 3,14-dimethoxy compound 19e: mp 290-294° C. (dec); TLC R$_f$ 0.35 (CHCl$_3$-MeOH, 95:5); $^1$H NMR (DMSO-d$_6$) δ 1.42-1.46 (m, 1H, C-15H), 2.16-2.63 (m, 5H, C-8H$_2$, C-10H, C-15H, C-16H), 2.33 (s, 3H, NCH$_3$), 3.01 (d, 1H, J=17.12 Hz, C-16H), 3.11 (s, 3H, C-14 OCH$_3$), 3.23-3.42 (m, 2H, C-10H, C-9H), 3.67 (s, 3H, C-3 OCH$_3$), 5.36 (s, 1H, C-5H), 6.65 (d, 1H, J=8.2 Hz, C-2H), 6.70 (d, 1H, J=8.2 Hz, C-1H), 7.52-7.57 (m, 2H, C-2'H, C-6"H), 7.71-7.74 (m, 2H, C-3'H, C-5"H), 7.77 (d, 1H, J=2.1 Hz, C-4'H), 8.78 (d, 1H, J=2.1 Hz, C-6'H). ESI MS m/z 475 (MH)$^+$.

Step 2.

The dimethoxy compound 19e (0.360 g, 0.76 mmol) was dissolved in anhydrous CH$_2$Cl$_2$ (15 mL), cooled to −78° C., and treated dropwise with boron tribromide (1M solution in CH$_2$Cl$_2$, 1.5 mL, 1.5 mmol). After maintaining the mixture at −78° C. for 1 h, it was allowed to warm to room temperature. The reaction was quenched by addition to ice cold water. The crude product was extracted with CHCl$_3$, dried over anhydrous sodium sulfate, the solvent was removed under reduced pressure and the crude product was purified by column chromatography over silica using CHCl$_3$-MeOH—NH$_4$OH 97.5:2:0.5 to obtain 0.12 g (35%) of 17e:

MP: 296-299° C. (dec.); TLC R$_f$ 0.23 (CHCl$_3$-MeOH, 95:5); $^1$H NMR (DMSO-d$_6$) δ 1.42-1.46 (m, 1H, C-15H), 1.70-2.63 (m, 5H, C-8H$_2$, C-10H, C-15H, C-16H), 2.35 (s, 3H, NCH$_3$), 3.00 (d, 1H, J=17.0 Hz, C-16H), 3.10 (s, 3H, C-14 OCH$_3$), 3.14-3.50 (m, 2H, C-10H, C-9H), 5.32 (s, 1H, C-5H), 6.49-6.56 (m, 2H, C-2H, C-1H), 7.52-7.57 (m, 2H, C-2"H, C-6"H), 7.71-7.74 (m, 2H, C-3"H, C-5"H), 7.77 (m, 1H, C-4'H), 8.78 (d, 1H, J=1.98 Hz, C-6'H), 9.05 (s, 1H, C-3 OH). ESI MS m/z 461 (MH)$^+$. Anal. (C$_{27}$H$_{25}$ClN$_2$O$_3$.0.25H$_2$O) C, H, N.

Example 6

14-Benzyloxy-5'-(4-chlorophenyl)-6,7-didehydro-4,5α-epoxy-3-hydroxy-17-methylpyrido[2',3':6,7]morphinan (17f)

Step 1.

To a stirred solution of 9 in DMF (10 mL) at 0° C. was added sodium hydride (0.288 g, 6.0 mmol, 60% dispersion in mineral oil, washed with hexane). After stirring at 0° C. for 20 min, benzyl bromide (0.425 g 6.0 mmol) was added and the mixture was stirred at room temperature overnight. The reaction mixture was cautiously treated with ice-cold water, diluted with water, and extracted with CHCl$_3$. The organic extracts were dried over anhydrous sodium sulfate, concentrated, and the residue obtained after removal of the solvent was purified over a column of silica using CHCl$_3$-MeOH 99:1 to obtain 0.57 g (Yield 46%) of 3,14-Bis(benzyloxy)-5'-(4-chlorophenyl)-6,7-didehydro-4,5α-epoxy-17-methylpyrido[2',3':6,7]morphinan (19f).

Step 2.

A solution of 19f (0.54 g, 1.0 mmol) was dissolved in anhydrous CH$_2$Cl$_2$ was cooled to −78° C. and treated dropwise with boron tribromide (3.0 mL, 1 M solution in CH$_2$Cl$_2$, 3.0 mmol). After allowing the mixture to stir at −78° C. for 1 h, it was allowed to warm to room temperature. The mixture was quenched by addition of water (10 mL), extracted with CHCl$_3$ (2×50 mL), dried and concentrated. The crude product thus obtained was purified chromatography over a column of silica using CHCl$_3$-MeOH 98:2 as the eluent. The product was crystallized from ethyl acetate to yield 0.12 g (23%) of the desired product (17f).

MP: 228-232° C.; TLC R$_f$ 0.5 (CHCl$_3$-MeOH, 92.5:7.5); $^1$H NMR (CDCl$_3$), δ 1.49-1.52 (m, 1H, C-15H), 2.21-2.28 (m, 1H, C-15H), 2.37 (s, 3H, NCH$_3$), 2.45-2.61 (m, 4H, C-16H$_2$, C-10H, C-8H), 3.12 (d, 1H, J=17.1 Hz, C-10H), 3.25 (s, 1H, C8H), 3.52 (d, 1H, J=5.5 Hz, C-9H), 4.37 (dd, 2H, J=11.5 and 11.4 Hz OCH$_2$), 5.32 (s, 1H, C-5H), 6.52-6.57 (m, 2H, C-1H, C-2H), 7.07-7.18 (5H, C$_6$H$_5$), 7.53-7.59 (m, 2H, C-3"H, 5"H), 7.69-7.73 (m, 3H, C-4'H, C-2"H, 6"H), 8.79 (d, 1H, J=1.95 Hz, C-6'H), 9.05 (s, 1H, C-3 OH). ESI MS m/z 537 (MH)$^+$. Anal. (C$_{33}$H$_{29}$ClN$_2$O$_3$.0.25.H$_2$O) C, H, N.

Example 7

5'-(4-Chlorophenyl)-14-cinnamyloxy-6,7-didehydro-4,5α-epoxy-3-hydroxy-17-methylpyrido[2',3':6,7]morphinan (17g)

Step 1.

Compound 20 (0.460 g, 1.0 mmol) was reacted with sodium hydride (0.144 g, 6.0 mmol, 60% dispersion in mineral oil) and cinnamyl bromide (0.202 g, 1.1 mmol) in DMF (15 mL) as described for in step 1 for 17e to obtain 0.18 g (31%) of 5'-(4-Chlorophenyl)-14-cinnamyloxy-6,7-didehydro-4,5α-epoxy-3-methoxy-17-methylpyrido[2',3':6,7]morphinan (19g): mp 210-212° C.; TLC R$_f$ 0.46 (CHCl$_3$-MeOH, 95:5); $^1$H NMR (DMSO-d$_6$) δ 1.46-1.51 (m, 1H, C-15H), 2.15-2.63 (2m, 5H, C-15H, C-8H, C-10H, C-16H$_2$), 2.36 (s, 3H, NCH$_3$), 3.05 (d, 1H, J=17.1 Hz, C-8H), 3.25-3.28 (m, 1H, C-10H), 3.45-3.49 (m, 1H, C-9H), 3.68 (s, 3H, C-3 OCH$_3$), 4.07-4.25 (m, 2H, CH$_2$CH=), 5.45 (s, 1H, C-5H), 6.08-6.30 (m, 2H, —CH=CH—), 6.67 (d, 1H, J=8.5 Hz, C-2H), 6.71 (d, 1H, J=8.2 Hz, C-1H), 7.12-7.25 (m, 5H, phenyl), 7.50 (dd, 2H, J=6.7 and 6.7 Hz, C-3"H, C-5"H), 7.60 (m, 2H, C-2"H, C-6"H), 7.71 (d, 1H, J=2.0 Hz, C-4'H), 8.75 (s, 1H, C-6'H). ESI MS m/z 577 (MH)$^+$.

Step 2.

Compound 19g (0.288 g, 0.5 mmol) was O-demethylated using boron tribromide and the product obtained after column chromatography using EtOAc-hexane (75:25) was crystallized from EtOAc to yield 0.102 g (57%) of the desired product 17g.

MP: 148-150° C.; TLC R$_f$ 0.33 (CHCl$_3$-MeOH, 90:10); $^1$H NMR (DMSO-d$_6$) δ 1.46-1.51 (m, 1H, C-15H), 2.20-2.66 (2m, 5H, C-15H, C-8H, C-10H, C-16H$_2$), 2.36 (s, 3H, NCH$_3$), 3.05 (d, 1H, J=17.1 Hz, C-8H), 3.22-3.28 (m, 1H, C-10H), 3.43-3.49 (m, 1H, C-9H) 4.07-4.25 (m, 2H, CH$_2$CH=), 5.41 (s, 1H, C-5H), 6.08-6.29 (m, 2H, CH=CH), 6.50-6.57 (m, 2H, C-2H, C-1H), 7.10-7.25 (m, 5H, C$_6$H$_5$), 7.46-7.52 (m, 2H, C-3"H, C-5"H), 7.62-7.68 (m, 2H, C-2"H, C-6"H), 7.71 (d, 1H, J=2.0 Hz, C-4'H), 8.78 (s, 1H, C-6'H), 9.07 (s, 1H, C-3 OH). ESI MS m/z 563 (MH)$^+$. Anal. (C$_{35}$H$_{31}$ClN$_2$O$_3$.0.75H$_2$O) C, H, N.

Example 8

5'-(4-Chlorophenyl)-6,7-didehydro-4,5α-epoxy-3-hydroxy-17-methyl-14-(3-phenylpropoxy)pyrido[2',3':6,7]morphinan (17h)

Step 1.

Compound 20 (0.96 g, 2.0 mmol) was reacted with sodium hydride (0.320 g, 4.0 mmol, 60% dispersion in mineral oil) and 3-phenylpropyl bromide (0.46 g, 2.6 mmol) in DMF (20 mL) as described in step 1 for 17e to obtain 0.28 g (24%) of 5'-(4-Chlorophenyl)-14-cinnamyloxy-6,7-didehydro-4,5α-epoxy-3-methoxy-17-methyl-14-(3-phenylpropoxy)pyrido[2',3':6,7]morphinan (19h). ESI MS m/z 579 (MH)$^+$.

Step 2.

Compound 19h (0.15 g, 0.26 mmol) was O-demethylated using boron tribromide to obtain 0.09 g (62%) of the desired product (17h).

MP: 128-130° C.; TLC R$_f$ 0.37 (CHCl$_3$-MeOH, 95:5); $^1$H NMR (DMSO-d$_6$) δ 1.39-1.53 (m, 1H, C-15H), 1.52-1.66 (m, 2H, CH$_2$CH$_2$Ph), 2.09-2.66 (m, 7H, CH$_2$Ph, C-16H$_2$, C-8H, C-10H, C-15H), 2.49 (s, 3H, NCH$_3$), 2.95 (d, 1H, J=16.81 Hz, C-8H), 3.15-3.72 (m, 4H, OCH$_2$, C-10H, C-9H), 5.38 (s, 1H, C-5H), 6.50 (s, 2H, C-2H, C-1H), 6.88-7.18 (m, 5H, C$_6$H$_5$), 7.48-7.58 (m, 2H, C-5"H, C-3"H), 7.65-7.75 (m, 3H, C-4'H, C-2"H, C-6"H), 8.8 (d, 1H, J=2.09 Hz, C-6'H), 9.04 (s, 1H, C-3 OH). ESI MS m/z 565 (MH). Anal. (C$_{35}$H$_{33}$ClN$_2$O$_3$.0.25H$_2$O) C, H, N.

Example 9

14-Benzoyloxy-5'-(4-chlorophenyl)-17-(cyclopropylmethyl)-6,7-didehydro-4,5α-epoxy-3-hydroxypyrido[2',3': 6,7]morphinan (18a)

To a solution of 6 (0.486 g, 1.0 mmol) in anhydrous DMF (10 mL), was added benzoyl chloride (0.421 g, 3.0 mmol) and triethylamine (0.42 mL). The reaction mixture was heated at 100° C. for 5 h under argon. The mixture was concentrated under reduced pressure, diluted with water, and extracted with CHCl$_3$. The organic extracts were dried over anhydrous sodium sulfate, filtered, and the filtrate was evaporated to dryness. The residue obtained was dissolved in methanol (24 mL) and treated with saturated aqueous K$_2$CO$_3$ to adjust the pH of the mixture to 9-10. The basic solution was stirred at room temperature for 3.5 hours. The mixture was then concentrated under reduced pressure, diluted with water, and extracted with CHCl$_3$. Workup of the extract and purification of the crude product on a column of silica using CHCl$_3$-MeOH 98:2 yielded 0.192 g (32%) of the desired product 18a.

MP: 158-162° C.; TLC R$_f$ 0.56 (CHCl$_3$-MeOH, 95:5); $^1$H NMR (DMSO-d$_6$) δ 0.07-0.17 and 0.32-0.35 (m, 4H, cyclopropyl CH$_2$CH$_2$), 0.58-0.62 (m, 1H, cyclopropyl CH), 1.67-1.71 (m, 1H, C-15H), 2.17-2.45 (m, 3H, NCH$_2$-cyclopropyl, C-15H), 2.63-2.82 (m, 4H, C-16H$_2$, C-10H, C-8H), 3.15 (d, 1H, J=18.5 Hz, C-10H), 3.54 (d, 1H, J=17.9 Hz, C-8H), 4.68 (d, 1H, J=6.0 Hz, C-9H), 5.71 (s, 1H, C-5H), 6.58 (s, 2H, C-1H, C-2H), 7.43-7.89 (m, 10H, C$_6$H$_5$, C-3"H, C-5"H, C-4'H, C-2"H, C-6"H), 8.82 (d, 1H, J=2.1 Hz, C-6'H), 9.15 (s, 1H, C-3 OH). ESI MS m/z 591 (MH)$^+$. Anal. (C$_{36}$H$_{31}$ClN$_2$O$_4$.0.5H$_2$O) C, H, N.

Example 10

5'-(4-Chlorophenyl)-17-(cyclopropylmethyl)-6,7-didehydro-4,5α-epoxy-3-hydroxy-14-(phenylacetoxy)pyrido[2',3':6,7]morphinan (18b)

This compound was prepared using the method described above for the preparation of 18a using toluene as the solvent instead of DMF. The reaction of 6 (0.486 g, 1.0 mmol), phenylacetyl chloride (0.50 g, 3.0 mmol) and triethylamine (0.6 mL) in toluene (10 mL) followed by basic workup of the reaction mixture and purification over a column of silica using EtOAc-hexane 60:40 yielded 0.101 g (17%) of the desired product 18b.

MP: 118-120° C.; TLC R$_f$ 0.46 (CHCl$_3$-MeOH, 92.5:7.5); $^1$H NMR (DMSO-d$_6$) δ 0.33-0.47 (m, 4H, cyclopropyl CH$_2$CH$_2$), 0.64-0.88 (m, 1H, cyclopropyl CH), 1.51 (d, 1H, J=10.3 Hz, C-15H), 2.08-2.72 (m, 7H, C-16H$_2$, C-15H, C-10H, C-8H, NCH$_2$), 3.05 (d, 1H, J=18.8 Hz, C-10H), 3.55-

3.70 (m, 3H, CH$_2$CO, C-8H), 4.51 (d, 1H, J=6.0 Hz, C-9H), 5.34 (s, 1H, C-5H), 6.53 (s, 2H, C-1H, C-2H), 6.92-7.06 (5H, C$_6$H$_5$), 7.53 (m, 2H, C-3"H, C-5"H), 7.62 (d, 1H, J=2.1 Hz, C-4'H), 7.62-7.72 (m, 2H, C-2"H, C-6"H), 8.81 (d, 1H, J=2.0 Hz, C-6'H), 9.14 (s, C-3 OH). ESI MS m/z 605 (MH). Anal. (C$_{37}$H$_{33}$ClN$_2$O$_4$.H$_2$O) C, H, N.

Example 11

5'-(4-Chlorophenyl)-17-(cyclopropylmethyl)-6,7-didehydro-4,5α-epoxy-3-hydroxy-14-(3-phenylpropionyloxy)pyrido[2',3':6,7]morphinan (18c)

This compound was prepared by using the method similar to that employed for the preparation of 18a. Yield 19%. mp 96-98° C.; TLC R$_f$ 0.47 (CHCl$_3$-MeOH, 95:5); $^1$H NMR (DMSO-d$_6$) δ 0.08-0.11 and 0.39-0.48 (m, 4H, cyclopropyl CH$_2$CH$_2$), 0.67-71 (m, 1H, cyclopropyl CH), 1.57 (d, 1H, J=10.7 Hz, C-15H), 2.15-2.25 (m, 2H, CH$_2$CH$_2$Ph), 2.37-2.80 (m, 9H, C-16H$_2$, C-15H, C-10H, C-8H, NCH$_2$a CH$_2$CH$_2$Ph), 3.08 (d, 1H, J=18.9 Hz, C-10H), 3.54 (d, 1H, J=17.6 Hz, C-8H), 4.48 (d, 1H, J=5.9 Hz, C-9H), 5.46 (s, 1H, C-5H), 6.55 (s, 2H, C-1H, C-2H), 6.98-7.16 (m, 5H, C$_6$H$_5$), 7.53-7.57 (m, 2H, C-3"H, 5"H), 7.71-7.75 (m, 3H, C-4'H, C-2"H, C-6"H), 8.86 (d, 1H, J=2.0 Hz, C-6'H), 9.11 (s, 1H, C-3OH). ESI MS m/z 618 (MH)$^+$. Anal. (C$_{38}$H$_{35}$ClN$_2$O$_4$.0.5H$_2$O) C, H, N.

Example 12

14-Benzoyloxy-5'-(4-chlorophenyl)-6,7-didehydro-4,5α-epoxy-3-hydroxy-17-methylpyrido[2',3':6,7]morphinan (18d)

This compound was prepared by reacting 9 (0.446 g, 1.0 mmol) with benzoyl chloride (0.425 g, 3.0 mmol) in the presence of triethylamine (0.62 mL, 5.0 mmol) in toluene (7 mL). Basic workup and purification of the reaction mixture yielded 0.068 g (12%) of the desired product.

MP: 280-284° C.; TLC R$_f$ 0.39 (CHCl$_3$-MeOH, 95:5); $^1$H NMR (CDCl$_3$) δ 1.68 (d, 1H, J=10.3 Hz, C-15H), 2.25 (s, 3H, NCH$_3$), 2.9 (d, 1H, J=3.3 Hz, C-15H), 2.60-2.83 (m, 4H, C-16 H$_2$, C-10H, C-8H), 3.26 (s, 1H, C-10H), 3.71 (d, 1H, J=17.4 Hz, C-8H), 4.36 (d, 11, J=6.1 Hz, C-9H), 5.72 (s, 1H, C-5H), 6.59-6.64 (m, 2H, C-1H, C-2H), 7.4-7.52 (m, 4H, 3"H, 5"H, m-protons of Bz), 7.54-7.62 (m, 1H, p-proton of Bz), 7.66-7.75 (m, 2H, C-2"H, C-6"H), 7.79 (d, 1H, J=1.94 Hz, C-4'H), 7.84-7.89 (m, 2H, C$_6$H$_5$), 8.81 (d, 1H, J=2.1 Hz, C-6'H), 9.16 (s, 1H, C-3 OH). ESI MS m/z 551 (MH)$^+$. Anal. (C$_{33}$H$_{27}$ClN$_2$O$_4$) C, H, N.

Example 13

5'-(4-Chlorophenyl)-6,7-didehydro-4,5α-epoxy-3-hydroxy-17-methyl-14-(phenylacetoxy)pyrido[2',3':6,7]morphinan (18e)

Prepared as described above for 18d using phenylacetyl chloride as the reagent. Yield 16%. mp 194-196° C.; TLC R$_f$ 0.68 (CHCl$_3$-MeOH, 92.5:7.5); $^1$H NMR (CDCl$_3$), δ 1.58 (d, 1H, J=10.3 Hz, C-15H), 2.25 (s, 3H, NCH$_3$), 1.20-2.83 (m, 5H, C-16H$_2$, C-15H, C-10H, C-8H), 3.26 (s, 1H, C-10H), 3.17 (d, 1H, J=18.5 Hz, C8H), 3.42-3.71 (m, 3H, CH$_2$Ph, C-8H), 4.15 (d, 1H, J=6.0 Hz, C-9H), 5.32 (s, 1H, C-5H), 6.53 (s, 2H, C-1H, C-2H), 6.93-7.06 (m, 5H, C$_6$H$_5$), 7.53 (m, 2H, J=2.0 Hz, C-3"H, 5"H), 7.61 (d, 1H, J=1.94 Hz, C-4'H), 7.68 (d, 2H, J=6.6 Hz, C-2"H, C-6"H), 8.81 (d, 1H, J=2.0 Hz, C-6'H). ESI MS m/z 565 (MH). Anal. (C$_{34}$H$_{29}$ClN$_2$O$_4$.0.25H$_2$O) C, H, N.

Example 14

5'-(4-Chlorophenyl)-6,7-didehydro-4,5α-epoxy-3-hydroxy-17-methyl-14-(3-phenylpropionyloxy)pyrido[2',3':6,7]morphinan (18f)

Prepared as described above for 18d using phenylpropionyl chloride as the reagent. Yield (22%): mp 242-244° C.; TLC R$_f$ 0.63 (CHCl$_3$-MeOH, 92.5:7.5); $^1$H NMR (CDCl$_3$), δ 1.55-1.59 (m, 1H, C-15H), 2.15-2.22 (m, 1H, C-15H), 2.25 (s, 3H, NCH$_3$), 2.38-2.76 (m, 8H, C-16H$_2$, C-15H, C-8H, CH$_2$CH$_2$Ph), 3.18 (d, 1H, J=19.8 Hz, C-10H), 3.50 (d, 1H, J=18.5 Hz, C-8H), 4.17 (d, 1H, J=6.0 Hz, C-9H), 5.45 (s, 1H, C-5H), 6.53 (s, 2H, C-1H, C-2H), 6.98-7.10 (m, 5H, C$_6$H$_5$), 7.54-7.57 (m, 2H, C-3"H, C-5"H), 7.71-7.76 (m, 3H, C-4'H, C-2"H, C-6"H), 8.85 (d, 1H, J=2.1 Hz, C-6'H), 9.11 (s, 1H, C-3 OH). ESI MS m/z 579 (MH)$^+$. Anal. (C$_{35}$H$_{31}$ClN$_2$O$_4$) C, H, N.

Example 15

3,14-Dibenzoyloxy-5'-(4-chlorophenyl)-17-(cyclopropylmethyl)-6,7-didehydro-4,5α-epoxy-3-hydroxypyrido[2',3':6,7]morphinan (21) and 3-Benzoyloxy-5'-(4-chlorophenyl)-17-(cyclopropylmethyl)-6,7,8,14-tetradehydro-4,5α-epoxypyrido[2',3':6,7]morphinan (22)

To a solution of 6 (0.972 g, 2.0 mmol) in anhydrous DMF (15 mL), and benzoyl chloride (1.2 g, 6.0 mmol) was added triethylamine (1.67 mL, 12.0 mmol). The reaction mixture was heated at 100° C. for 5 h under argon. The mixture was cooled, diluted with H$_2$O (150 mL) and the product was extracted with CHCl$_3$. The organic extracts were washed with water and brine and dried over anhydrous sodium sulfate. The residue obtained after the removal of the solvent under reduced pressure was chromatographed over a column of silica using EtOAc-hexane 60:40 as the eluent. Collection of fractions containing the faster moving component and workup gave 21.

Yield 0.67 g (48%). TLC R$_f$ 0.74 (CHCl$_3$-MeOH, 98.5:2.5); $^1$H NMR (DMSO-d$_6$) δ 0.022-0.075 and 0.34-0.40 (m, 4H, cyclopropyl CH$_2$CH$_2$), 0.55-0.67 (m, 1H, cyclopropyl CH), 1.74-1.85 (m, 1H, C-15H), 2.21-2.48 (m, 1H, C-15H), 2.22-2.48 (m, 2H, NCH$_2$-cyclopropyl), 2.72-2.96 (m, 4H, C-16H$_2$, C-10H$_2$, C-8H), 3.28-3.40 (s, 1H, C-8H), 3.84 (d, 1H, J=17.6 Hz, C-10H), 4.78 (d, 1H, J=6.0 Hz, C-9H), 5.89 (s, 1H, C-5H), 6.87 (d, 1H, J=8.2 Hz, C-1H), 7.02 (d, 1H, J=6.2 Hz, C-2H), 7.42-7.57 (m, 4H, m-protons of 3-Bz, C-3"H, C-5"H), 7.52-7.66 (m, 3H, m- and p-protons of 14-Bz), 7.72-7.82 (m, 3H, p-protons of 14-Bz, C-2"H, C-6"H), 7.86 (d, 1H, J=1.7 Hz C-4'H), 7.90-7.94 (m, 2H, o-protons of 14-Bz), 8.09-8.20 (m, 2H, o-protons of C-3 Bz), 8.81 (m, 1H, C-6'H). ESI MS m/z 695 (MH)$^+$ Anal. (C$_{43}$H$_{35}$ClN$_2$O$_5$.0.25H$_2$O) C, H, N.

Elution and workup of the slower moving component gave 22: Yield 0.48 g (35%). mp 132-134° C.; TLC R$_f$ 0.58 (CHCl$_3$-MeOH, 95:5); $^1$H NMR (DMSO-d$_6$) δ 0.15-0.19 and 0.50-0.54 (m, 4H, cyclopropyl CH$_2$CH$_2$), 0.85-0.91 (m, 1H, cyclopropyl CH), δ 1.77 (d, J=11.7 Hz, 1H, C-15H), 2.30-2.37 (m, 1H, C-15H), 2.5-2.58 (m, 2H, NCH$_2$-cyclopropyl), 2.76-2.94 (m, 3H, C-16H$_2$, C-10H), 3.46 (s, 1H, C-10H), 4.41 (d, 1H, J=7.0 Hz, C-9H), 5.88 (s, 1H, C-5H), 6.31 (s, 1H, C-8H), 6.73 (d, 1H, J=8.3 Hz, C-2H), 6.95 (d, 1H, J=8.2

C-1H), 7.55-7.78 (m, 7H, m- and p-protons of C-3 Bz and C-3″H, C-5″H, C-2″H, C-6″H), 7.85 (d, 1H, J=2.2 Hz, C-4′H), 8.10-8.11 (m, 2H, o-protons of C3-Bz), 8.72 (d, 1H, J=2.1 Hz, C-6′H). ESI MS m/z 573 (MH)$^+$. Anal. ($C_{36}H_{29}ClN_2O_3 \cdot 0.75H_2O$) C, H, N.

Example 16

5′-(4-Chlorophenyl)-17-(cyclopropylmethyl)-3-hydroxy-6,7,8,14-tetradehydro-4,5α-epoxypyrido[2′,3′:6,7]morphinan (23)

A solution of 22 (0.42 g, 0.73 mmol) was dissolved in MeOH (14 mL) and saturated aqueous $K_2CO_3$ was added dropwise to adjust the pH of the solution to 9-10. The mixture was stirred at room temperature for 3.5 h, diluted with $H_2O$, and extracted with $CHCl_3$. The organic extracts were dried over anhydrous sodium sulfate, filtered, and concentrated under reduced pressure. The residue obtained was purified by chromatography over a column of silica using $CHCl_3$-MeOH 98:2 as the eluent to obtain 0.25 g (74%) of 23: mp 164-166° C.; TLC $R_f$ 0.38 ($CHCl_3$-MeOH, 95:5); $^1$H NMR (DMSO-$d_6$) δ 0.01-0.17 and 0.47-0.54 (m, 4H, cyclopropyl $CH_2CH_2$), 0.82-0.89 (m, 1H, cyclopropyl CH), 1.70 (d, 1H, J=12.1 Hz, C-15H), 2.23-2.25 (m, 1H, C-15H), 2.45-2.47 (m, 2H, C-8H2), 2.70-2.89 (m, 3H, C-16H2, C-10H), 3.16-3.21 (d, 1H, J=18.0 Hz, C-10H), 4.04-4.10 (m, 1H, C-9H), 5.74 (s, 1H, C-5H), 6.20 (s, 1H, C-8H), 6.45-6.52 (m, 2H, C-1H, C-2H), 7.55-7.57 (m, 2H, C-3″H, C-5″H), 7.71-7.75 (m, 3H, C-4′H, C-2″H, C-6″H), 8.76 (d, 1H, J=2.2 Hz, C-6′H), 9.13 (s, 1H, C-3 OH). ESI MS m/z 469 (MH)$^+$. Anal. ($C_{29}H_{25}ClN_2O_2 \cdot 0.75H_2O$) C, H, N.

Ligand Binding at the Opioid Receptors. All target compounds were evaluated for binding affinities at DOR, MOR and KOR using a radioligand displacement assay with membranes prepared from CHO cells stably expressing these receptors. The radioligands [3H]DADLE, [$^3$H]DAMGO and [$^3$H]U69,593 were used for labeling the DOR, MOR and KOR sites, respectively. These evaluations were performed as previously described. (See Fontana et al., Synthetic studies of neoclerodane diterpenoids from *Salvia splendens* and evaluation of Opioid Receptor affinity. Tetrahedron 2008, 64, 10041-10048. Rothman et al., Allosteric interactions at the m-opioid receptor. J. Pharmacol. Exp. Ther. 2007, 320, 801-810. Xu et al., A comparison of noninternalizing (herkinorin) and internalizing (DAMGO) μ-opioid agonists on cellular markers related to opioid tolerance and dependence. Synapse 2007, 61, 166-175.) The affinity and selectivity data for the target compounds are given in Table 1. With the exception of 18a and 18d, all of the ligands displayed high affinity binding at DOR with $K_i$<5 nM. In general, all of the ligands displayed relatively non-selective binding profiles at all three opioid receptor subtypes. The 14-methoxy compound 17a arising from 14-O-methylation displayed a binding profile somewhat similar to that of the parent compound 6. In contrast, methylation of 9 produced the ligand 17e that displayed markedly improved binding affinity at MOR and KOR. Among the N-CPM compounds, installation of the arylalkyl groups such as benzyl, cinnamyl and phenethyl on the oxygen at C-14 (compounds 17b, 17c, and 17d) consistently increased the binding affinity at MOR. A similar trend of increasing MOR affinity is seen among the N-Me compounds 17e, 17f, and 17g. Placement of a benzoyloxy group at C-14 is generally not well tolerated. The two benzoyloxy compounds 18a and 18d are 45- and 10-fold weaker in binding to DOR compared to their 14-benzyloxy counterparts, 17b and 17f, respectively. These benzoyloxy ligands also displayed comparable decrease in affinity at MOR and KOR indicating a general unfavorable interaction trend among all receptor subtypes. In contrast, installation of phenylacetyl and phenylpropionyl groups (18b, 18c, 18e and 18f) gave ligands with moderate to high affinity at all three receptors. In fact the phenylpropoxy and phenylpropionyl ligands possessing three atom separation between 14-O and the pendant phenyl group (17d vs 18c and 17h vs 18f) display somewhat comparable affinity profiles. The relatively high affinity of these ligands at all three receptors may be attributable to the conformational flexibility afforded by the longer chain to position the pendant phenyl group to occupy a suitable binding pocket for favorable hydrophobic or aryl-π interactions at the ligand binding pocket. The binding profile of compound 23 lacking an ether function with unsaturation between C-8 and C-14 resembles that of the saturated (6) or the methoxy (17a) analogues exhibiting lower affinity at MOR compared to affinities at DOR and KOR.

TABLE 1

Binding Affinities of the Pyridomorphinans at DOR, MOR and KOR

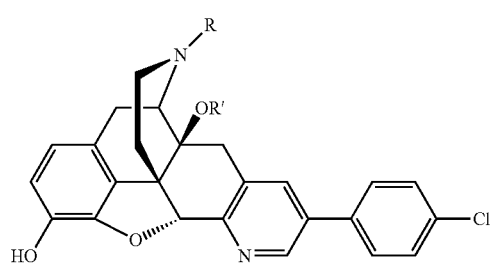

| | | | $K_i$ ± SEM (nM) | | | selectivity ratio | |
| --- | --- | --- | --- | --- | --- | --- | --- |
| compd | R | R' | DOR$^a$ | MOR$^b$ | KOR$^c$ | MOR/DOR | KOR/DOR |
| 17a | CPM | Me | 1.95 ± 0.14 | 41.9 ± 2.8 | 5.37 ± 0.48 | 22 | 2.8 |
| 17b | CPM | $C_6H_5CH_2$ | 1.91 ± 0.08 | 8.42 ± 0.29 | 5.33 ± 0.27 | 4.4 | 2.8 |
| 17c | CPM | $C_6H_5CH=CHCH_2$ | 3.74 ± 0.32 | 3.03 ± 0.38 | 3.31 ± 0.30 | 0.81 | 0.89 |
| 17d | CPM | $C_6H_5CH_2CH_2CH_2$ | 1.20 ± 0.12 | 0.66 ± 0.06 | 1.82 ± 0.11 | 0.55 | 1.5 |
| 17e | Me | Me | 1.63 ± 0.08 | 7.89 ± 0.33 | 27.99 ± 1.59 | 4.8 | 17 |
| 17f | Me | $C_6H_5CH_2$ | 1.78 ± 0.15 | 4.69 ± 0.17 | 49.0 ± 6.0 | 2.6 | 28 |
| 17g | Me | $C_6H_5CH=CHCH_2$ | 1.14 ± 0.11 | 0.41 ± 0.04 | 1.55 ± 0.09 | 0.36 | 1.4 |

TABLE 1-continued

Binding Affinities of the Pyridomorphinans at DOR, MOR and KOR

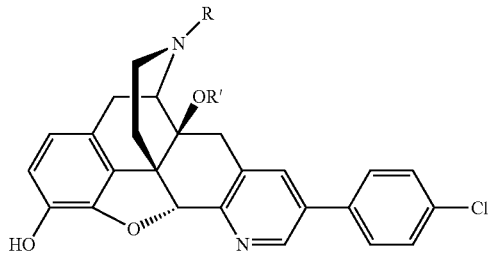

| compd | R | R' | $K_i$ ± SEM (nM) | | | selectivity ratio | |
| --- | --- | --- | --- | --- | --- | --- | --- |
| | | | DOR[a] | MOR[b] | KOR[c] | MOR/DOR | KOR/DOR |
| 17h | Me | $C_6H_5CH_2CH_2CH_2$ | 1.04 ± 0.08 | 0.54 ± 0.04 | 1.53 ± 0.10 | 0.52 | 1.5 |
| 18a | CPM | $C_6H_5CO$ | 87 ± 8 | 192 ± 21 | 117 ± 6 | 2.2 | 1.3 |
| 18b | CPM | $C_6H_5CH_2CO$ | 1.33 ± 0.10 | 1.04 ± 0.25 | 3.10 ± 0.19 | 0.78 | 2.3 |
| 18c | CPM | $C_6H_5CH_2CH_2CO$ | 4.13 ± 0.29 | 2.58 ± 0.12 | 12.0 ± 13 | 0.62 | 2.9 |
| 18d | Me | $C_6H_5CO$ | 17.0 ± 1.0 | 84.0 ± 7.0 | 112 ± 4 | 4.9 | 6.6 |
| 18e | Me | $C_6H_5CH_2CO$ | 0.97 ± 0.04 | 1.43 ± 0.08 | 17.0 ± 1.0 | 1.5 | 18 |
| 18f | Me | $C_6H_5CH_2CH_2CO$ | 0.96 ± 0.05 | 0.94 ± 0.05 | 4.41 ± 0.23 | 0.98 | 4.6 |
| 23 | CPM | — | 2.71 ± 0.11 | 13.0 ± 0.4 | 5.97 ± 0.19 | 4.8 | 2.2 |
| 6[d] | CPM | H | 2.20 ± 0.20 | 51.0 ± 8.0 | 20.0 ± 1.0 | 23 | 9 |
| 9[d] | Me | H | 3.90 ± 0.20 | 230 ± 10 | 468 ± 17 | 59 | 120 |

[a]Displacement of [³H]DADLE from CHO cell membrane expressing DOR.
[b]Displacement of [³H]DAMGO from CHO cell membranes expressing hMOR.
[c]Displacement of [³H]U69,593 from CHO cells expressing hKOR.
[d]Data using brain tissue membranes included for comparison.

In Vitro Functional Activity at the Opioid Receptors.

Compound selections and in vitro functional activity determinations were performed with the primary aim of identifying ligands possessing the desired mixed MOR agonist/DOR antagonist activity. The agonist efficacy ($E_{max}$) and potency ($EC_{50}$) values were determined using previously described [³⁵S]GTP-γ-S binding assays with cells expressing MOR, DOR or KOR. The agonist $E_{max}$ values were normalized to the stimulation produced by the standard agonists DAMGO, DADLE and U69,593 at MOR, DOR and KOR, respectively. The antagonist potency of the ligands was determined using a [³⁵S]GTP-γ-S binding assay by measuring the shift in $EC_{50}$ value of standard agonists. The functional activity data thus obtained are presented in Table 2. With the exception of 18d, all of the compounds 17e-h, 18e and 18f possessing the classical MOR agonist N-Me structural feature displayed full agonist efficacy at MOR with $E_{max}$ values>100. The weak MOR agonist potency and partial efficacy of 18d is in conformity with its poor binding affinity at MOR. In terms of agonist potency; whereas, the methyl and benzyl ethers were weak (17e, $EC_{50}$=379 nM; 17f, $EC_{50}$=301 nM), the cinnamyl (17g) and the 3-phenylpropyl (17h) ethers were nearly 100-fold more potent with $EC_{50}$ values of 4.27 nM and 2.15 nM, respectively. Compared to these ethers, the esters displayed diminished MOR agonist potencies (18e $EC_{50}$=87 nM; 18f $EC_{50}$=48 nM). All of the esters (18a-c) as well as the unsaturated compound 23 possessing the classical antagonist N-CPM structural feature did indeed turn out to be antagonists at MOR. Similarly, the methyl, benzyl and cinnamyl ethers 17a-c possessing the N-CPM group also displayed a non-agonist profile at MOR. Most interestingly, however, the phenylpropyl ether 17d possessing the N-CPM group displayed an agonist profile at MOR ($E_{max}$=72%, $EC_{50}$=1.74 nM). This transformative influence on the functional activity at MOR brought about by installation of a 3-phenylpropoxy group at the 14-position of the 17-cyclopropylmethyl-4,5-epoxypyridomorphinan is similar to the effect of such a group on 17-cyclopropylmethyl-4,5-epoxy-6-oxomorphinans.

It has been demonstrated that pyridomorphinans in general, and those possessing an aryl group such as the 4-chlorophenyl group at the 5'-position on the pyridine ring in particular, showed a non-agonist functional profile at DOR, irrespective of whether the ligands possessed a MOR-agonist methyl group (9 and 10) or a MOR-antagonist CPM group (6 and 8) on the morphinan nitrogen. The functional activity profile of the current series of compounds at DOR, however, is influenced by the nature of the substituent at C-14. In the current series of compounds, all of the ligands possessing an N-CPM group were antagonists at DOR including 17d. However, ligands possessing N-methyl group (17f, 17g, 17h, 18e and 18f) displayed weak to potent partial agonist activity at DOR. Among the N-methyl compounds, the 14-methoxy compound 17e is the only exception retaining antagonist activity at DOR. The N-CPM containing MOR agonist ligand 17d also turned out to be the most potent DOR antagonist with a $K_e$ of 0.091 nM.

At KOR, most of the tested ligands displayed weak partial agonist activity ($E_{max}$<36%) with varying potencies as antagonists. The phenylpropoxy compound 17d was devoid of agonist activity at KOR. Thus, the incorporation of the phenylpropoxy group on a pyridomorphinan possessing the N-CPM group did not induce agonist activity at DOR or KOR as it did at MOR. This is in contrast to the results from incorporation of a phenylpropoxy group on 6-oxomorphinans reported by Schmidhammer and coworkers, who found that introduction of a phenylpropoxy group at the C14-position of naltrexone (1) yielded the agonist 13, devoid of any antagonist activity. (see Greiner et al., Synthesis and biological evaluation of 14-alkoxymorphinans. 18. N-substituted 14-phenylpropyloxymorphinan-6-ones with unanticipated agonist properties: extending the scope of common structure-activity relationships. J. Med. Chem. 2003, 46, 1758-1763.)

Among the compounds of the present disclosure, 17d emerged as a compound of particular interest as it displayed a balanced profile of potent agonist activity at MOR coupled with antagonist activity at DOR and KOR.

TABLE 2

Functional Activity of the Pyridomorphinans at DOR, MOR and KOR.

| | antagonist activity | | | agonist activity | | | | | |
|---|---|---|---|---|---|---|---|---|---|
| compd | DOR $K_e$ (nM) | MOR $K_e$ (nM) | KOR $K_e$ (nM) | DOR $EC_{50}$ (nM) | DOR $E_{max}$ (%) | MOR $EC_{50}$ (nM) | MOR $E_{max}$ (%) | KOR $EC_{50}$ (nM) | KOR $E_{max}$ (%) |
| 17a | a | a | a | no stim[b] | na[c] | no stim | na | a | a |
| 17b | 0.64 ± 0.11 | 11 ± 1 | 13 ± 3 | no stim | na | no stim | na | 27 ± 9 | 15 ± 1 |
| 17c | a | a | a | no stim | na | no stim | na | a | a |
| 17d | 0.091 ± 0.01 | d | 1.35 ± 0.28 | no stim | na | 1.74 ± 0.20 | 72 ± 2 | no stim | na |
| 17e | 1.60 ± 0.35 | d | 17 ± 0.13 | no stim | na | 379 ± 50 | 118 ± 4 | 633 ± 108 | 36 ± 2 |
| 17f | 4.54 ± 0.81 | d | 83 ± 14 | 11 ± 1 | 52 ± 1 | 301 ± 28 | 119 ± 3 | 215 ± 54 | 32 ± 2 |
| 17g | e | e | e | 0.59 ± 0.05 | 84 ± 2.0 | 4.27 ± 0.57 | 130 ± 3 | e | e |
| 17h | e | e | 6.9 ± 0.02 | 0.27 ± 0.03 | 85 ± 2.0 | 2.15 ± 0.21 | 125 ± 2 | no stim | na |
| 18a | 218 ± 2 | 261 ± 36 | 126 ± 13 | no stim | na | no stim | na | no stim | na |
| 18b | 0.37 ± 0.04 | 0.48 ± 0.06 | 7 ± 2 | no stim | na | no stim | na | 26 ± 9 | 34 ± 2 |
| 18c | 1.86 ± 0.21 | 13 ± 1.7 | 14 ± 2 | no stim | na | no stim | na | 13 ± 4 | 25 ± 1 |
| 18d | 45 ± 6 | 1273 ± 166 | 426 ± 47 | no stim | na | 4623 ± 1439 | 55 ± 8 | no stim | na |
| 18e | 3.38 ± 0.34 | d | 198 ± 20 | 19 ± 6 | 27 ± 3 | 87 ± 10 | 122 ± 3 | 109 ± 24 | 36 ± 2 |
| 18f | 1.64 ± 0.30 | d | 18 ± 0.2 | 5.52 ± 0.53 | 59 ± 2 | 48 ± 5 | 105 ± 2 | 136 ± 60 | 16 ± 2 |
| 23 | 0.58 ± 0.10 | 8.0 ± 0.89 | 19 ± 3.0 | no stim | na | no stim | na | no stim | na | a Not tested due to lack of agonist activity at MOR.
[b]No stimulation of [$^{35}$S]GTP-γ-S binding at 10 mM.
[c]Not applicable.
d Not tested due to full agonist activity at MOR.
e Not tested due to agonist activity at both MOR and DOR.

In Vitro Studies on Tolerance and Dependence.

Two experiments using CHO cells co-expressing MOR and DOR (dimer cells) to determine the effect of 17d on the development of tolerance and dependence, respectively. As a control, the MOR/DOR dual agonist 17h was used in these experiments. Dimer cells were treated for 20 h with medium (control), morphine (1 μM), 17d (30 nM) or 17h (30 nM). These concentrations were chosen to be approximately 25-fold greater than the corresponding $EC_{50}$ values for stimulation of [$^{35}$S]GTP-γ-S binding to membranes prepared from dimer cells. As reported in FIG. 1, chronic morphine and chronic 17h resulted in an ~7-fold increase in the $EC_{50}$ value for DAMGO-mediated inhibition of forskolin-stimulated cAMP accumulation. Unlike morphine, 17d and 17h decreased the $E_{max}$ value for DAMGO-mediated inhibition of forskolin-stimulated cAMP by 40% and 20%, respectively.

Figure 2:
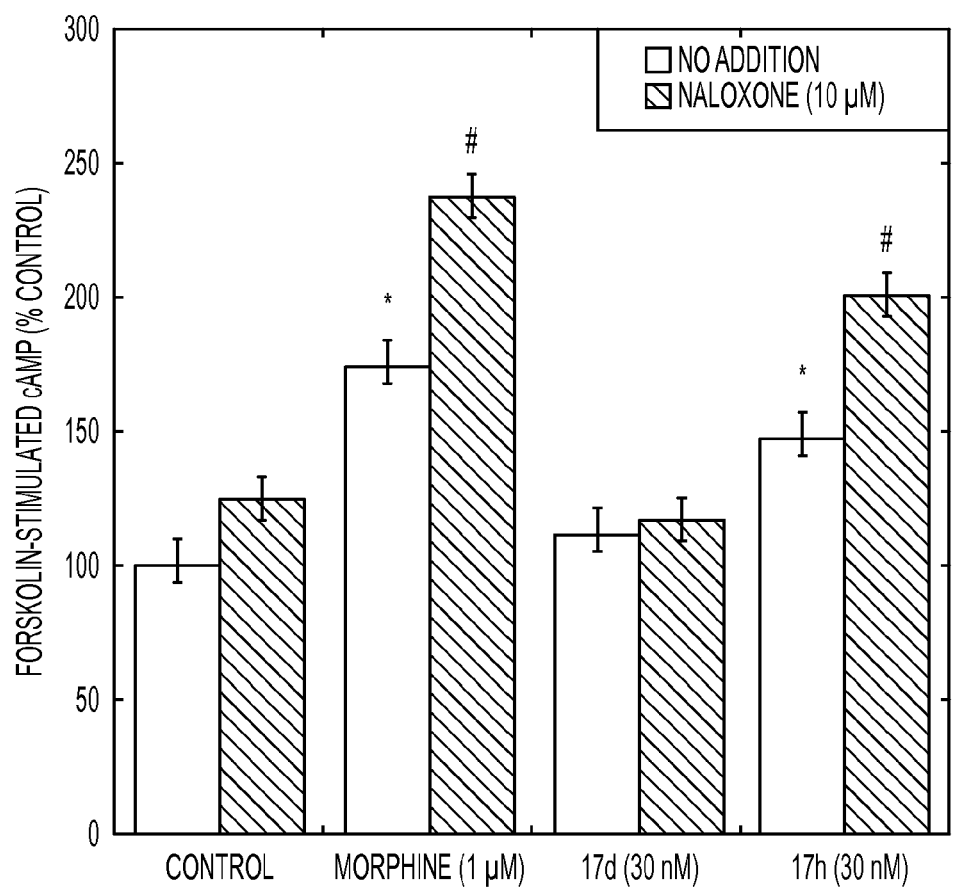
FIG. 2 is a graph showing the "dependence" experiments of dimer cells that were treated chronically as described in the treatments in FIG. 1.

In the "dependence" experiments (FIG. 2), dimer cells were treated chronically as described above. After 20 h treatment, the cells were washed to remove drugs, and the degree of cAMP accumulation produced by forskolin/IBMX (100 μM/500 μM) was determined in the absence and presence of 10 μM naloxone. Chronic morphine produced a significant increase in forskolin-stimulated cAMP accumulation, a phenomenon called "cAMP superactivation". The combination of forskolin plus naloxone produced a further increase in cAMP accumulation, a phenomenon called "naloxone-induced cAMP overshoot." The MOR agonist/DOR agonist compound (17h) produced effects similar to that of morphine, whereas the MOR agonist/DOR antagonist compound (17d) did not.

Chronic treatment of cells that express MOR with MOR agonists produce a variety of cellular adaptations that together produce tolerance and dependence. See Waldhoer et al., Opioid receptors. Annu. Rev. Biochem. 2004, 73, 953-990. Three such changes were assessed: 1) tolerance, as determined by shifts in the DAMGO-dose response curve for inhibition of forskolin-stimulated cAMP accumulation, 2) cAMP superactivation and 3) the naloxone-induced cAMP overshoot. These latter two measures are generally considered as cellular signs related to dependence. The cAMP overshoot reflects the formation of constitutively active receptors, which are receptors that activate G proteins in the absence of an agonist. The constitutively active MORs decrease forskolin-stimulated cAMP, and naloxone, as an inverse agonist, decreases the activity of the constitutively active MORs, thereby relieving the inhibition. The net result is a further increase in forskolin-stimulated cAMP accumulation.

The results observed here with chronic morphine treatment of dimer cells are similar to what was observed previously using CHO cells that stably express the cloned human MOR. Xu et al., A comparison of noninternalizing (herkinorin) and internalizing (DAMGO) μ-opioid agonists on cellular markers related to opioid tolerance and dependence. Synapse 2007, 61, 166-175. In contrast, chronic treatment of dimer cells with the MOR agonist/DOR antagonist 17d did not produce either tolerance, as defined as an increase in the $EC_{50}$ value for DAMGO-mediated inhibition of forskolin-stimulated cAMP, or dependence, as defined by the presence of cAMP superactivation or a naloxone-induced cAMP overshoot. The MOR agonist/DOR agonist 17h had similar effects to that of morphine.

These data support the hypothesis that the mu/delta heterodimer may be a crucial mediator of tolerance and dependence. See Waldhoer et al., A heterodimer-selective agonist shows in vivo relevance of G protein-coupled receptor dimers. Proc. Natl. Acad. Sci. U.S.A. 2005, 102, 9050-9055.

Analgesic Activity and Tolerance Studies in Mice.

Figure 3A:
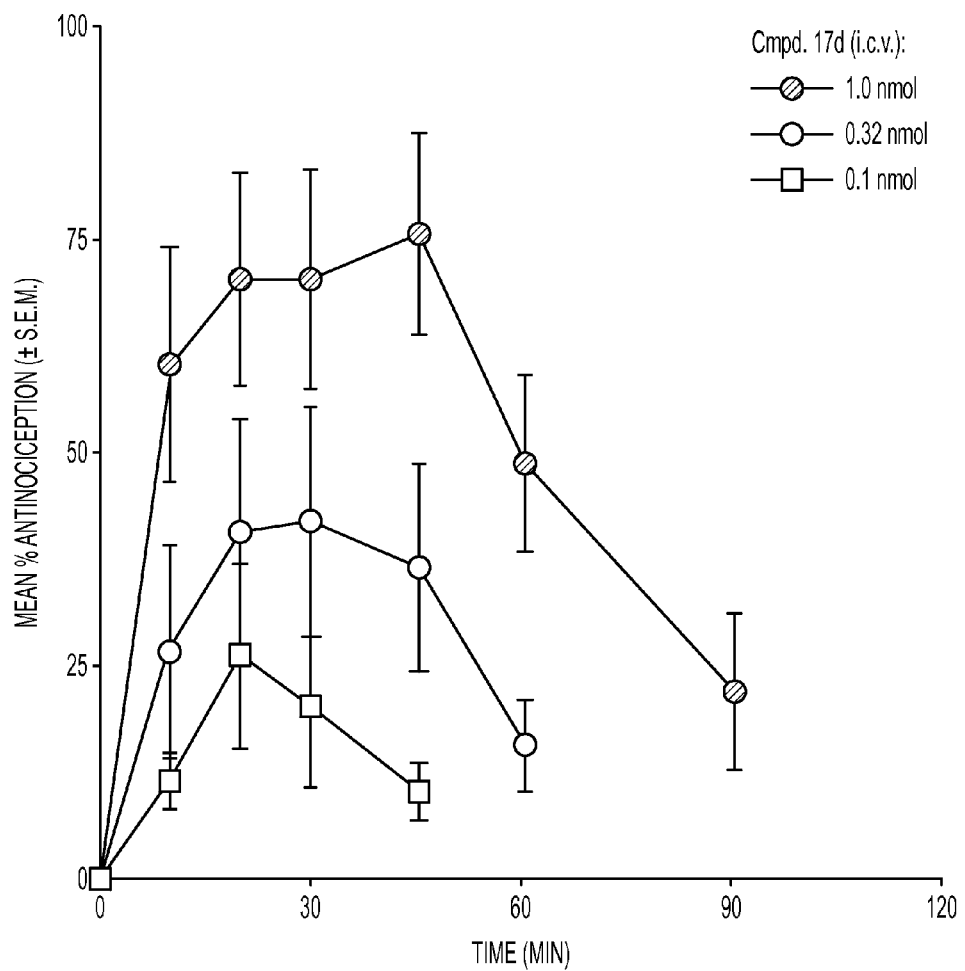
FIGS. 3A and 3B are graphs showing antinociceptive dose- and time-response curves for exemplified compounds of the present disclosure.
Figure 3B:
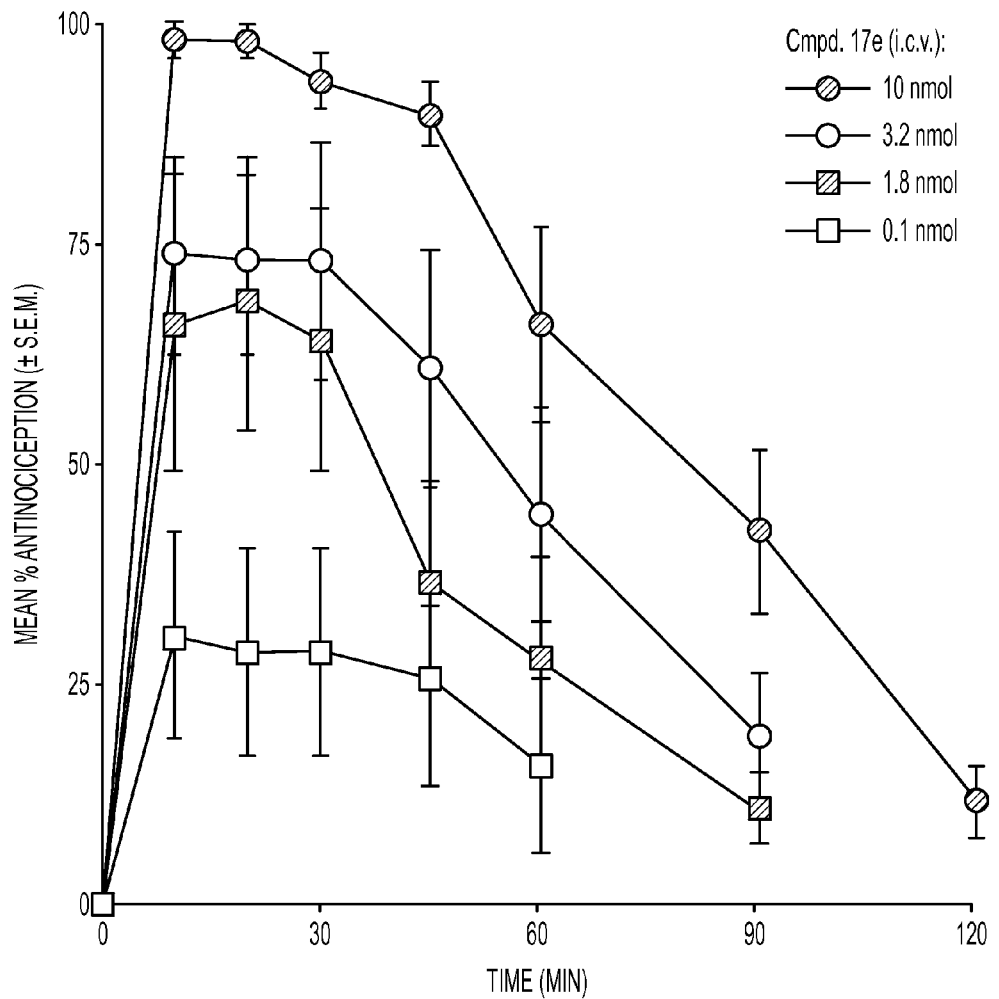
Figure 4A:
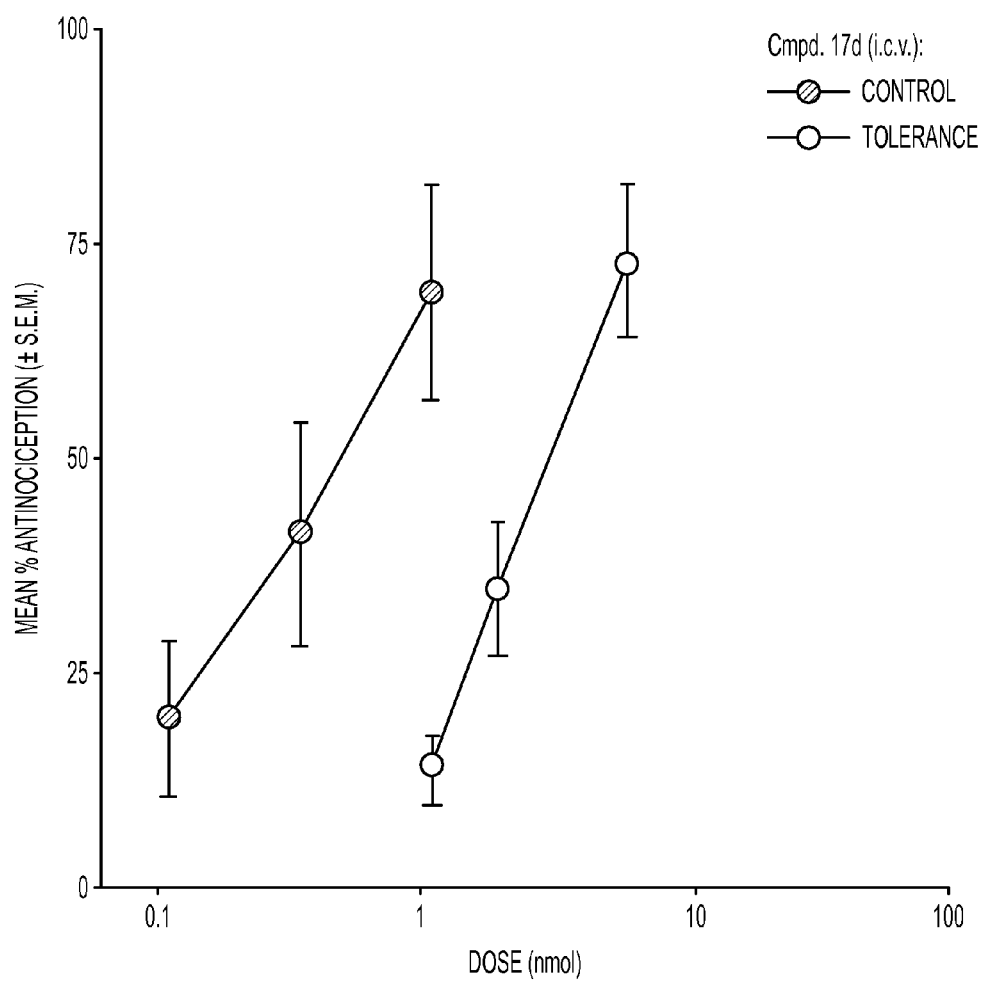
FIGS. 4A and 4B are graphs showing antinociceptive dose-response curves for naïve control mice and mice injected repeatedly with exemplified compounds of the present disclosure.
Figure 4B:
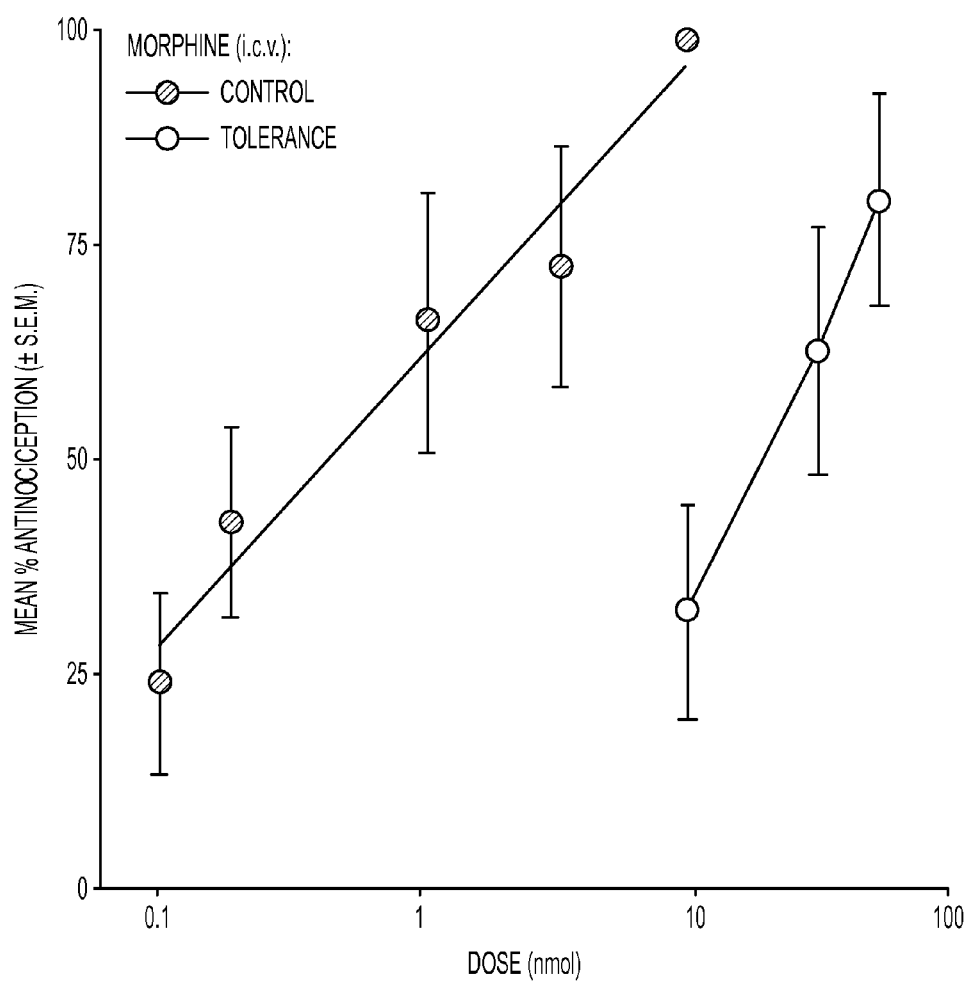

The analgesic activity of selected ligands were tested in mice using the 55° C. warm-water tail-withdrawal test as described previously. See Wells et al., In vivo pharmacological characterization of SoRI 9409, a nonpeptidic opioid mu-agonist/delta-antagonist that produces limited antinociceptive tolerance and attenuates morphine physical dependence. J. Pharmacol. Exp. Ther. 2001, 297, 597-605. Compounds that were evaluated were 17d, 17e, 17g, and 17h. These compounds were administered by the intracerebroventricular (icv) route. All of the tested compounds produced full antinociceptive effects. The antinociceptive effects of these compounds were blocked by naloxone pretreatment confirming that the analgesic activity of these compounds is mediated through opioid receptors. The antinociceptive dose-response curves for 17d and 17e are shown in FIGS. 3A and 3B, respectively. The calculated antinociceptive $A_{50}$ values of all the tested compounds and the morphine control are listed in Table 3. In this assay, compounds 17d, 17g, and 17h displayed potency equivalent to or better than that of morphine. This is attributable to potent agonist activity of these ligands at MOR (17d) or at both MOR and DOR (17g and 17h) as determined in the [$^{35}$S]GTP-γ-S assays. Despite the very weak MOR agonist potency displayed by 17e in the [$^{35}$S]GTP-γ-S assay (MOR agonist $EC_{50}$=379 nM), this compound produced significant analgesic effect and was only 6-fold weaker than other tested ligands. As evaluated in the in vitro tolerance assays, it was of interest to determine the effects of two compounds, 17d, a MOR agonist/DOR antagonist and 17h, a MOR-DOR dual agonist. The studies were carried out using the tolerance development assay involving repeated injection of the test compound for 3 days twice daily. The degree of tolerance development is indicated by the fold-shift in the antinociceptive $A_{50}$ values when tested in naïve control mice and in the repeated injection paradigm. In this repeated administration paradigm, morphine produces a significant development of tolerance inducing a 45-fold shift in $A_{50}$ value. Compared to morphine, the mixed MOR agonist/DOR antagonist ligand displayed only 7.9-fold shift in antinociceptive potency, thus confirming that this ligand indeed produces significantly less tolerance than morphine (FIGS. 4A and 4B). Based on the results from the in vitro tolerance study, the MOR-DOR dual agonist ligand 1.7h might be expected to display robust tolerance development in the repeated injection paradigm. Unfortunately, undue toxicity displayed by this compound on repeated administration precluded the determination of induction of analgesic tolerance.

TABLE 3

Analgesic Activity of Selected Ligands in the Mouse Warm-Water Tail-Withdrawal Assay[a]

| compd | Antinociceptive $A_{50}$ Values | 95% confidence limits |
| --- | --- | --- |
| 17d | 0.35 nmol | 0.18-0.69 nmol |
| 17e | 1.44 nmol | 1.02-2.03 nmol |
| 17g | 0.23 nmol | 0.16-0.33 nmol |
| 17h | 0.23 nmol | 0.18-0.30 nmol |
| morphine | 0.43 nmol | 0.38-0.51 nmol |

[a]Compounds were administered icv and the $A_{50}$ values calculated at time of peak effect.

Pharmacological evaluations with the mixed MOR agonist/DOR antagonist ligand 17d demonstrated that the mixed function ligand indeed produces diminished tolerance and dependence effects in a cellular model system as compared to the MOR/DOR dual agonist ligand 17h. Moreover, the MOR agonist/DOR antagonist 17d, when tested using the repeated administration procedure in mice produced greatly diminished tolerance development as compared to morphine.

Opioid Binding Assays.

As described (Fontana et al., Synthetic studies of neoclerodane diterpenoids from *Salvia splendens* and evaluation of Opioid Receptor affinity. Tetrahedron 2008, 64, 10041-10048.), the recombinant CHO cells (hMOR-CHO, hDOR-CHO and hKOR-CHO) were produced by stable transfection with the respective human opioid receptor cDNA The cells were grown on plastic flasks in DMEM (90%) (hDOR-CHO and hKOR-CHO) or DMEM/F-12 (45%/45%) medium (hMOR-CHO) containing 10% FetalClone II (HyClone) and Geneticin (G-418: 0.10-0.2 mg/ml) (Invitrogen) under 95% air/5% $CO_2$ at 37° C. Cell monolayers were harvested and frozen in –80° C. The hKOR-CHO, hMOR-CHO and hDOR-CHO cells are used for opioid binding experiments. For the [$^{35}$S]GTP-γ-S binding experiments, hKOR-CHO and hMOR-CHO cells were used for assaying KOR and MOR receptor function. The NG108-15 neuroblastoma×glioma cell for the DOR [$^{35}$S]GTP-γ-S binding assay was used. In summary, the hDOR-CHO cells for DOR binding assays was used, and the NG108-15 cells for the DOR [$^{35}$S]GTP-γ-S binding assay.

[$^{3}$H][D-Ala$^{2}$-MePhe$^{4}$,Gly-ol$^{5}$]enkephalin ([$^{3}$H]DAMGO, SA=44-48 Ci/mmol) was used to label MOR, [3H][D-Ala$^{2}$, D-Leu$^{5}$]enkephalin ([$^{3}$H]DADLE, SA=40-50 Ci/mmol) to label DOR and [$^{3}$H](–)-U69,593 (SA=50 Ci/mmol) to label KOR binding sites. On the day of the assay, cell pellets were thawed on ice for 15 minutes then homogenized with a polytron in 10 mL/pellet of ice-cold 10 mM Tris-HCl, pH 7.4. Membranes were then centrifuged at 30,000×g for 10 minutes, resuspended in 10 mL/pellet ice-cold 10 mM Tris-HCl, pH 7.4 and again centrifuged 30,000×g for 10 min. Membranes were then resuspended in 25° C. 50 mM Tris-HCl, pH 7.4 (~100 mL/pellet hMOR-CHO, 50 mL/pellet hDOR-CHO and 120 mL/pellet hKOR-CHO). All assays took place in 50 mM Tris-HCl, pH 7.4, with a protease inhibitor cocktail [bacitracin (100 μg/mL), bestatin (10 μg/mL), leupeptin (4 μg/mL) and chymostatin (2 μg/mL)], in a final assay volume of 1.0 mL. All drug dilution curves were made up with buffer containing 1 mg/mL BSA. Nonspecific binding was determined using 20 μM levallorphan ([3H]DAMGO and [$^{3}$H]DADLE) and 1 μM (–)-U69,593 (for [$^{3}$H]U69,593 binding). [$^{3}$H]Radioligands were used at ~2 nM concentrations. Triplicate samples were filtered with Brandel Cell Harvesters (Biomedical Research & Development Inc., Gaithersburg, Md.), over Whatman GF/B filters, after a 2 hr incubation at 25° C. The filters were punched into 24-well plates to which was added 0.6 mL of LSC-cocktail (Cytoscint). Samples were counted, after an overnight extraction, in a Trilux liquid scintillation counter at 44% efficiency. Opioid binding assays had ~30 μg protein per assay tube. Inhibition curves were generated by displacing a single concentration of radio ligand by 10 concentrations of drug.

[$^{35}$S]GTP-γ-S Binding Assays.

The [$^{35}$S]GTP-γ-S assays were conducted as described by Fontana et al., Synthetic studies of neoclerodane diterpenoids from *Salvia splendens* and evaluation of Opioid Receptor affinity. Tetrahedron 2008, 64, 10041-10048. In this description, buffer "A" is 50 mM Tris-HCl, pH 7.4, containing 100 mM NaCl, 10 mM $MgCl_2$, 1 mM EDTA and buffer "B" is buffer A plus 1.67 mM DTT and 0.15% BSA. On the day of the assay, cells were thawed on ice for 15 min and homogenized using a polytron in 50 mM Tris-HCl, pH 7.4, containing 4 μg/mL leupeptin, 2 μg/mL chymostatin, 10 μg/mL bestatin and 100 μg/mL bacitracin. The homogenate was centrifuged at 30,000×g for 10 min at 4° C., and the supernatant discarded. The membrane pellets were resuspended in buffer B and used for [$^{35}$S]GTP-γ-S binding assays. [$^{35}$S]GTP-γ-S binding was determined as described previously. Briefly, test tubes received the following additions: 50 μL buffer A plus 0.1% BSA, 50 μL GDP in buffer A/0.1% BSA (final concentration=40 μM), 50 μL drug in buffer A/0.1% BSA, 50 μL [$^{35}$S]GTP-γ-S in buffer A/0.1% BSA (final concentration=50 μM), and 300 μL of cell membranes (50 μg of protein) in buffer B. The final concentrations of reagents in the [$^{35}$S]GTP-γ-S binding assays were: 50 mM Tris-HCl, pH 7.4, containing 100 mM NaCl, 10 mM MgCl$_2$, 1 mM EDTA, 1 mM DTT, 40 µM GDP and 0.1% BSA. Incubations proceeded for 3 h at 25° C. Nonspecific binding was determined using GTP-γ-S (40 µM). Bound and free [$^{35}$S]GTP-γ-S were separated by vacuum filtration (Brandel) through GF/B filters. The filters were punched into 24-well plates to which was added 0.6 mL LSC-cocktail (Cytoscint). Samples were counted, after an overnight extraction, in a Trilux liquid scintillation counter at 27% efficiency.

Data Analysis and Statistics.

These methods are described in Rothman et al., A: Allosteric interactions at the µ-opioid receptor. J. Pharmacol. Exp. Ther. 2007, 320, 801-810 and Xu et al., A comparison of noninternalizing (herkinorin) and internalizing (DAMGO) µ-opioid agonists on cellular markers related to opioid tolerance and dependence. Synapse 2007, 61, 166-175. For opioid binding experiments, the pooled data of three experiments (typically 30 data points) are fit to the two-parameter logistic equation for the best-fit estimates of the IC$_{50}$ and N values: Y=100/(1+([INHIBITOR]/IC$_{50}$)N), where "Y" is the percent of control value. K$_i$ values for test drugs are calculated according to the standard equation: K$_i$=IC$_{50}$/(1+[radioligand]/Kd]). For the [$^3$H]radioligands, the following Kd values (nM±SD, n=3) were used in the K$_i$ calculation: [$^3$H]DAMGO (0.93±0.04), [$^3$H]DADLE (1.9±0.3) and [$^3$H](−)-U69,593 (11±0.6). The corresponding B$_{max}$ values were (fmol/mg protein±SD, n=3): [$^3$H]DAMGO (1912±68), [$^3$H]DADLE (3655±391) and [$^3$H](−)-U69,593 (3320±364).

For the [$^{35}$S]GTP-γ-S binding experiments, the percent stimulation of [$^{35}$S]GTP-γ-S binding was calculated according to the following formula: (S−B)/B×100, where B is the basal level of [$^{35}$S]GTP-γ-S binding and S is the stimulated level of [$^{35}$S]GTP-γ-S binding. Agonist dose-response curves (ten points/curve) are generated, and the data of several experiments, 3 or more, are pooled. The EC$_{50}$ values (the concentration that produces fifty percent maximal stimulation of [$^3$S]GTP-γ-S binding) and E$_{max}$ are determined using either the program MLAB-PC (Civilized Software, Bethesda, Md.), KaleidaGraph (Version 3.6.4, Synergy Software, Reading, Pa.) or Prism 4.0 (GraphPad Software, Inc, San Diego, Calif.). In most cases, the percent stimulation of the test compound is reported as a percent of the maximal stimulation of 1000 nM DAMGO, 500 nM SNC80 or 500 nM (−)-U50, 488 in the appropriate cell type. For determination of K$_e$ values using the "shift" experimental design, agonist (DAMGO, (−)-U50,488 or SNC80) dose-response curves are generated, using the appropriate cell type, in the absence and presence (ten points/curve) of a test compound. The data of several experiments, 3 or more, are pooled, and the K$_e$ values are calculated according to the equation: [Test Drug]/(EC$_{50-2}$/EC$_{50-1}$−1), where EC$_{50-2}$ is the EC$_{50}$ value in the presence of the test drug and EC$_{50-1}$ is the value in the absence of the test drug.

Cell Culture and cAMP Assay.

CHO cells co-expressing cloned µ and δ opioid receptors (cMyc-mδ-HµCHO cells) were produced by stable transfection with the mouse δ opioid receptor with N-cMyc tag and human µ opioid receptor cDNA. Cells were grown on plastic flasks in F-12 Nutrient Mixture (HAM, GIBCO) containing 10% fetal bovine serum, 100 units/mL penicillin, 100 µg/mL streptomycin, 400 µg/mL hygromycin B (for δ receptor selection), and 400 µg/mL geneticin (for v receptor selection) under 95% air/5% CO$_2$ at 37° C. After 80% confluence, cell monolayers were plated in 24-well plates and grown in F-12 Nutrient Mixture (HAM, GIBCO) containing 10% fetal bovine serum, 100 units/mL penicillin, 100 µg/mL streptomycin, 400 µg/mL hygromycin B and 400 µg/mL geneticin under 95% air/5% CO$_2$ at 37° C. On the day of the experiment, cells (control or drug-treated) were washed three times with serum free medium, and incubated with serum free medium, containing IBMX (500 µM). After a 20-min incubation at 37° C., medium was removed and then cells incubated with fresh serum free medium containing IBMX (500 µM) and forskolin (100 µM) and appropriate agonist or antagonist for 15 min (assay for opioid inhibition of cAMP accumulation) or 10 min (assay for naloxone-induced cAMP overshoot) at 37° C. The reaction was terminated by aspiration of the medium and the addition of 0.5 mL of 0.1 N HCl. After chilling plates at 4° C. for at least 1 h, 0.4 mL was removed, neutralized, vortexed and centrifuged at 13,000 rpm for 5 min, supernatants were used for cAMP assay. These assay monitored inhibition of [$^3$H]cAMP binding to cAMP-dependent protein kinase. Assays took place in 50 mM Tris-HCl, pH 7.4, containing 100 mM NaCl and 5 mM EDTA. After a 2 h incubation at 4° C. (protected from light), bound and free [$^3$H]cAMP were separated by vacuum filtration through Whatman GF/B filters with two 4 mL washes with ice-cold 10 mM Tris-HCl, pH 7.4. Filters were punched into wells of plate to which was added 0.6 mL LSC-cocktail (CytoScint) and counted in a liquid scintillation counter at 44% efficiency.

Data Analysis and Statistics.

The amount of cAMP in the samples was quantitated from a cAMP standard curve ranging from 0.25 to 256 pmol of cAMP/assay. Forskolin (100 µM) stimulated cAMP formation in the absence of agonist was defined as 100%. The EC$_{50}$ (the concentration of agonist that produces fifty percent inhibition of forskolin stimulated cAMP formation) and E$_{max}$ (% of maximal inhibition of forskolin stimulated cAMP) were calculated using program Prizm version 4 (GraphPad Software, San Diego, Calif.). Data from three experiments were analyzed using the program Prizm version 4 (GraphPad Software, San Diego, Calif.). Results are presented as the mean±S.E.M.

Antinociceptive Studies.

Male ICR mice (Harlan) were used for all evaluations. Mice were housed in a temperature and humidity controlled vivarium on a 12:12 h light:dark cycle with unlimited access to food and water prior to the formal procedures. (Wells et al., In vivo pharmacological characterization of SoRI 9409, a nonpeptidic opioid mu-agonist/delta-antagonist that produces limited antinociceptive tolerance and attenuates morphine physical dependence. J. Pharmacol. Exp. Ther. 2001, 297, 597-605.) Graded doses of morphine or the test compounds were injected intracerebroventricularly (icv) under light ether anesthesia. Morphine sulfate was dissolved in distilled water and injected in a volume of 5 µL. The test compounds were dissolved in 100% DMSO and injected in a volume of 5 µL. Antinociceptive assays were performed at various times after injection.

Warm-Water Tail-Withdrawal Assay.

Naive mice were baselined in the 55° C. warm-water tail-withdrawal test as previously described by Wells et al., In vivo pharmacological characterization of SoRI 9409, a nonpeptidic opioid mu-agonist/delta-antagonist that produces limited antinociceptive tolerance and attenuates morphine physical dependence. J. Pharmacol. Exp. Ther. 2001, 297, 597-605 and Bilsky et al., Competitive and non-competitive NMDA antagonists block the development of antinociceptive tolerance to morphine, but not to selective mu or delta opioid agonists in mice. Pain 1996, 68, 229-237. Doses of morphine or the test compound were injected icv, and antinociception was assessed at 10, 20, 30, 45, 60, 80, 120 and 180 min post injection. Percent antinociception was calculated using the formula: % MPE (maximal possible effect)=100×(test−control)/(cutoff−control) where control is the predrug observation, test is the post drug observation, and cutoff is the maximal length of stimulus allowed (10 s for 55° C. tail-withdrawal). Antinociceptive $A_{50}$ values and 95% confidence intervals were determined using linear regression software (FlashCalc). Opioid activity of the test compounds was assessed by pretreating animals with naloxone (10 mg/kg ip, −10 min) followed by an icv injection of an approximate $A_{90}$ dose of test compound. If a compound did not produce a full agonist effect, then the dose that produced the greatest antinociceptive effect was used. Antinociception was assessed in the 55° C. warm-water tail-withdrawal test at 10, 20 and 30 min. A positive response to a fixed dose of naloxone was indicated when greater than 80% reduction in the antinociceptive effect of the agonist was observed.

Tolerance Regimen.

Mice were injected twice daily (8 a.m. and 8 p.m.) with an approximate $A_{90}$ dose of morphine or $A_{90}$ dose of 17d for 3 days. Antinociceptive dose-response curves in the warm-water tail-withdrawal assay were generated on the morning of the fourth day using the procedures outlined above.

In keeping with the present disclosure, the compounds of the present disclosure can be used alone or in appropriate association, and also may be used in combination with pharmaceutically acceptable carriers and other pharmaceutically active compounds. The active agent may be present in the pharmaceutical composition in any suitable quantity.

The pharmaceutically acceptable carriers described herein, for example, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices.

The choice of carrier will be determined in part by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, intraperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granule; (c) powders; (d) suspensions in an appropriate liquid; and (e) suitable emulsions. Liquid formulations may include diluents, such as water, cyclodextrin, dimethyl sulfoxide and alcohols, for example, ethanol, benzyl alcohol, propylene glycol, glycerin, and the polyethylene alcohols including polyethylene glycol, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, the addition to the active ingredient in an inert base, such as gelatin and glycerin, or sucrose and acadia, emulsions, and gels containing, in addition to the active ingredient, such carriers as are known in the art.

The compounds alone or in combination with other suitable components, can be made into aerosol formulations to be administered via inhalation. These aerosol formulations can be placed into pressurized acceptable propellants, such as dichlorodifluoromethane, propane, and nitrogen. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl β-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present disclosure. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The formulations can be presented in unit-does or multi-dose scaled containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art. See *Pharmaceutics and Pharmacy Practice*, J.B. Lippincott Co., Philadelphia, Pa., Banker and Chalmers, Eds., 238-250 (1982) and *ASHP Handbook on Injectable Drugs*, Toissel, 4$^{th}$ ed., 622-630 (1986).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, and gels containing, in addition to the active ingredient, such carriers as are known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

One skilled in the art will appreciate that suitable methods of exogenously administering a compound of the present disclosure to an animal are available, and, although more than one route can be used to administer a particular compound, a particular route can provide a more immediate and more effective reaction than another route.

As regards these applications, the present method includes the administration to an animal, particularly a mammal, and more particularly a human, of a therapeutically effective amount of the compound effective in the treatment of a condition that is capable of treatment with an agonist and/or antagonist of the opioid receptors. The dose administered to an animal, particularly a human, in the context of the present invention should be sufficient to affect a therapeutic response in the animal over a reasonable time frame. One skilled in the art will recognize that dosage will depend upon a variety of factors including the condition of the animal, the body weight of the animal, as well as the severity and stage of the cancer.

The total amount of the compound of the present disclosure administered in a typical treatment is preferably between about 10 mg/kg and about 1000 mg/kg of body weight for mice, and between about 100 mg/kg and about 500 mg/kg of body weight, and more preferably between 200 mg/kg and about 400 mg/kg of body weight for humans per daily dose. This total amount is typically, but not necessarily, administered as a series of smaller doses over a period of about one time per day to about three times per day for about 24 months, and preferably over a period of twice per day for about 12 months.

The size of the dose also will be determined by the route, timing and frequency of administration as well as the existence, nature and extent of any adverse side effects that might accompany the administration of the compound and the desired physiological effect. It will be appreciated by one of skill in the art that various conditions or disease states, in particular chronic conditions or disease states, may require prolonged treatment involving multiple administrations. Exemplary embodiments of the present disclosure include:

Embodiment A

A compound represented by the formula:

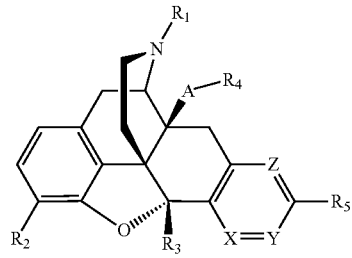

wherein $R_1$ is selected from the group consisting of H, linear or branched $C_{1-6}$ alkyl, $C_{3-7}$ cycloalkyl, cycloalkylalkyl having 3-7 carbon atoms in the cycloalkyl ring, each of the latter three groups being optionally substituted by a hydroxyl group when C≥2, $C_{3-4}$ alkenyl, aryl, arylalkyl, heterocycloalkyl or $(CH_2)_nCOR$, wherein n is 0 to 5 and R represents linear or branched $C_{1-6}$ alkyl, hydroxyl, $C_{1-5}$ alkoxy, $OC_{3-6}$ alkenyl or arylalkyl or heterocycloalkyl, $NR_6R_7$ where $R_6$ and $R_7$ may be the same or different, and each is H, linear or branched $C_{1-6}$ alkyl, cycloalkylalkyl having 3-7 carbon atoms in the cycloalkyl ring, $C_{3-5}$ alkenyl, aryl, heterocyclo, arylalkyl or heterocycloalkyl; or $R_1$ is a group D-E wherein D represents $C_{1-10}$ alkylene and E represents substituted or unsubstituted aryl or heterocyclo;

$R_2$ is selected from the group consisting of H, linear or branched $C_{1-6}$ alkyl, hydroxyl, $C_{1-5}$ alkoxy, halogen, and $(CH_2)_nCOR$, where n an R have the same meaning as described above, $SR_6$, nitro, $NR_6R_7$, $NHCOR_6$, $NHSO_2R_6$, $R_6$ and $R_7$ have the same meanings as described above, $R_3$ is hydrogen or $C_{1-6}$ alkyl;

$R_4$ is selected from the group consisting of H, linear or branched $C_{1-6}$ alkyl, cycloalkylalkyl having 3-7 carbon atoms in the cycloalkyl ring, $C_{3-5}$ alkenyl, aryl, heterocyclo, arylalkyl, and heterocycloalkyl; or $R_4$ is a group D-E wherein D represents $C_{1-10}$ alkylene and E represents substituted or unsubstituted aryl or heterocyclo; or $COR_6$;

A is selected from the group consisting of O, S, $NR_6$ and $CH_2$;

X is N;

Y is selected from the group consisting of N, $CR_6$ and $CCOR_6$;

Z is selected from the group consisting of N, CR$_6$ and CCOR$_6$; and
R$_5$ is selected from the group consisting of R$_6$ and COR$_6$;
pharmaceutically salt thereof, deuterium forms thereof, isomers thereof, solvate thereof and mixture thereof.

Embodiment B

A compound represented by the formula:

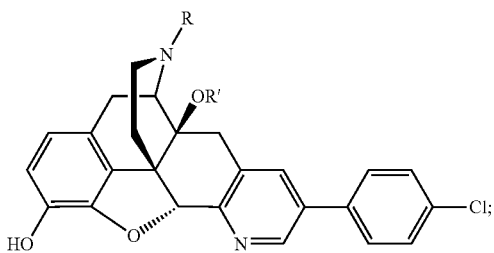

wherein R is cyclopropylmethyl or methyl and R' is alkyl or acyl, pharmaceutically acceptable salt thereof, deuterium forms thereof, isomers thereof, solvate thereof and mixture thereof.

Embodiment C

A compound selected from the group consisting of:
5'-(4-Chlorophenyl)-17-(cyclopropylmethyl)-6,7-didehydro-4,5α-epoxy-3-hydroxy-14-methoxypyrido[2',3':6,7]morphinan;
14-(Benzyloxy)-5'-(4-chlorophenyl)-17-(cyclopropylmethyl)-6,7-didehydro-4,5α-epoxy-3-hydroxypyrido[2',3':6,7]morphinan,
5'-(4-Chlorophenyl)-14-cinnamyloxy-17-(cyclopropylmethyl)-6,7-didehydro-4,5α-epoxy-3-hydroxypyrido[2',3':6,7]morphinan,
5'-(4-Chlorophenyl)-17-(cyclopropylmethyl)-6,7-didehydro-4,5α-epoxy-3-hydroxy-14-(3-phenylpropoxy)pyrido[2',3':6,7]morphinan,
5'-(4-Chlorophenyl)-6,7-didehydro-4,5α-epoxy-3-hydroxy-14-methoxy-17-methylpyrido[2',3':6,7]morphinan,
14-Benzyloxy-5'-(4-chlorophenyl)-6,7-didehydro-4,5α-epoxy-3-hydroxy-17-methylpyrido[2',3':6,7]morphinan,
5'-(4-Chlorophenyl)-14-cinnamyloxy-6,7-didehydro-4,5α-epoxy-3-hydroxy-17-methylpyrido[2',3':6,7]morphinan,
5'-(4-Chlorophenyl)-6,7-didehydro-4,5α-epoxy-3-hydroxy-17-methyl-14-(3-phenylpropoxy)pyrido[2',3':6,7]morphinan,
14-Benzoyloxy-5'-(4-chlorophenyl)-17-(cyclopropylmethyl)-6,7-didehydro-4,5α-epoxy-3-hydroxypyrido[2',3': 6,7]morphinan,
5'-(4-Chlorophenyl)-17-(cyclopropylmethyl)-6,7-didehydro-4,5α-epoxy-3-hydroxy-14-(3-phenylacetoxy)pyrido[2',3':6,7]morphinan,
5'-(4-Chlorophenyl)-17-(cyclopropylmethyl)-6,7-didehydro-4,5α-epoxy-3-hydroxy-14-(3-phenylpropionyloxy) pyrido[2',3':6,7]morphinan,
14-Benzoyloxy-5'-(4-chlorophenyl)-6,7-didehydro-4,5α-epoxy-3-hydroxy-17-methylpyrido[2',3':6,7]morphinan,
5'-(4-Chlorophenyl)-6,7-didehydro-4,5α-epoxy-3-hydroxy-17-methyl-14-(phenylacetoxy)pyrido[2',3':6,7]morphinan,
5'-(4-Chlorophenyl)-6,7-didehydro-4,5α-epoxy-3-hydroxy-17-methyl-14-(3-phenylpropionyloxy)pyrido[2',3':6,7] morphinan,
3,14-Dibenzoyloxy-5'-(4-chlorophenyl)-17-(cyclopropylmethyl)-6,7-didehydro-4,5α-epoxy-3-hydroxypyrido[2',3': 6,7]morphinan,
3-Benzoyloxy-5'-(4-chlorophenyl)-17-(cyclopropylmethyl)-6,7,8,14-tetradehydro-4,5α-epoxypyrido[2',3':6,7]morphinan, and
5'-(4-Chlorophenyl)-17-(cyclopropylmethyl)-3-hydroxy-6,7,8,14-tetradehydro-4,5α-epoxypyrido[2',3':6,7]morphinan,
pharmaceutically acceptable salt thereof, deuterium forms thereof, isomers thereof, solvate thereof and mixture thereof and solvate thereof.

Embodiment D

A pharmaceutical composition comprising a compound according to Embodiment A, B or C, pharmaceutically acceptable salts thereof, prodrugs thereof, deuterated forms thereof, isomers thereof, solvates thereof and mixtures thereof and a pharmaceutically acceptable carrier.

Embodiment E

A method for treating a patient suffering from a condition that is capable of treatment with an agonist and/or antagonist of the opioid receptors which comprises administering to said patient an effective amount of at least one compound or composition according to Embodiment A, B, C, or D, pharmaceutically salt thereof, deuterium forms thereof, isomers thereof, solvate thereof and mixture thereof.

Embodiment F

A method for treating a patient suffering from pain which comprises administering to the patient a pain treating effective amount of at least one compound or composition according to Embodiment A, B, C, or D, pharmaceutically salt thereof, deuterium forms thereof, isomers thereof, solvate thereof and mixture thereof.

Embodiment G

A method for treating a patient in need of an immunosuppressant to prevent rejection in organ transplant and skin graft, in need of an anti-allergic agent, in need of an anti-inflammatory agent, in need of a brain cell protectant, for drug and/or alcohol abuse, to decrease gastric secretion, for diarrhea, for cardiovascular disease, for a respiratory disease, in need of a cough and/or respiratory depressant, for mental illness, for epileptic seizures and other neurologic disorders which comprising administering to said patient an effective amount of at least one compound or composition according to Embodiment A, B, C, or D, pharmaceutically salt thereof, deuterium forms thereof, isomers thereof, solvate thereof and mixture thereof.

Embodiment H

A process for the preparation of any one of the compounds according to Embodiment A, B or C, pharmaceutically salt thereof, deuterium forms thereof, isomers thereof, solvate thereof and mixture thereof which comprises subjecting a 17-substituted-3,14-dihydroxypyridomorphinan to dialkylation at the phenolic hydroxyl at the 3-position and the tertiary alcohol at the 14-position followed by selective dealkylation of the phenolic ether function.

The term "comprising" (and its grammatical variations) as used herein is used in the inclusive sense of "having" or "including" and not in the exclusive sense of "consisting only of." The terms "a", "an" and "the" as used herein are understood to encompass the plural as well as the singular, unless indicated otherwise.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

What is claimed is:

1. A compound represented by the formula:

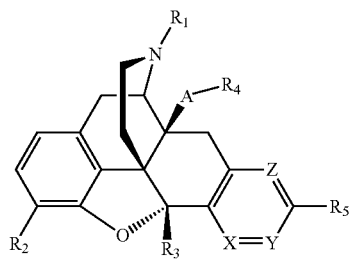

wherein $R_1$ is selected from the group consisting of linear or branched $C_{1-6}$ alkyl, cycloalkylalkyl having 3-7 carbon atoms in the cycloalkyl ring, or arylalkyl;

$R_2$ is selected from the group consisting of hydroxyl and methoxy, $R_3$ is hydrogen or methyl;

$R_4$ is selected from the group consisting of linear or branched $C_{1-6}$ alkyl, cycloalkylalkyl having 3-7 carbon atoms in the cycloalkyl ring, $C_{3-5}$ alkenyl, 3-aryl-2-propenyl, 3-heteroaryl-2-propenyl, arylalkyl heterocycloalkyl and $COR_6$;

A is selected from the group consisting of O, NH and $CH_2$;

X is N;

Y is selected from the group consisting of N, $CR_6$ and $CCOR_6$;

Z is selected from the group consisting of N, $CR_6$ and $CCOR_6$;

$R_5$ is selected from the group consisting of $R_6$ and $COR_6$; and $R_6$ is selected from the group consisting of H, linear or branched $C_{1-6}$ alkyl, cycloalkylalkyl having 3-7 carbon atoms in the cycloalkyl ring, $C_{3-5}$ alkenyl, aryl, heterocyclo, arylalkyl or heterocycloalkyl;

pharmaceutically salt thereof, deuterium forms thereof, isomers thereof, and mixture thereof.

2. The compound of claim 1 being represented by the formula:

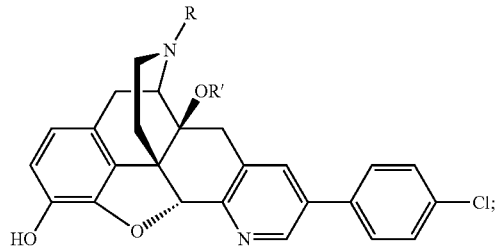

wherein R is cyclopropylmethyl or methyl and R' is alkyl or acyl, pharmaceutically acceptable salt thereof, deuterium forms thereof, isomers thereof, and mixture thereof.

3. The compound of claim 1 being selected from the group consisting of:

5'-(4-Chlorophenyl)-17-(cyclopropylmethyl)-6,7-didehydro-4,5α-epoxy-3-hydroxy-14-methoxypyrido[2',3':6,7]morphinan;

14-(Benzyloxy)-5'-(4-chlorophenyl)-17-(cyclopropylmethyl)-6,7-didehydro-4,5α-epoxy-3-hydroxypyrido[2',3':6,7]morphinan, 5'-(4-Chlorophenyl)-14-cinnamyloxy-17-(cyclopropylmethyl)-6,7-didehydro-4,5α-epoxy-3-hydroxypyrido[2',3':6,7]morphinan, 5'-(4-Chlorophenyl)-17-(cyclopropylmethyl)-6,7-didehydro-4,5α-epoxy-3-hydroxy-14-(3-phenylpropoxy)pyrido[2',3':6,7]morphinan, 5'-(4-Chlorophenyl)-6,7-didehydro-4,5α-epoxy-3-hydroxy-14-methoxy-17-methylpyrido[2',3':6,7]morphinan, 14-Benzyloxy-5'-(4-chlorophenyl)-6,7-didehydro-4,5α-epoxy-3-hydroxy-17-methylpyrido[2',3':6,7]morphinan, 5'-(4-Chlorophenyl)-14-cinnamyloxy-6,7-didehydro-4,5α-epoxy-3-hydroxy-17-methylpyrido[2',3':6,7]morphinan, 5'-(4-Chlorophenyl)-6,7-didehydro-4,5α-epoxy-3-hydroxy-17-methyl-14-(3-phenylpropoxy)pyrido[2',3':6,7]morphinan, 14-Benzoyloxy-5'-(4-chlorophenyl)-17-(cyclopropylmethyl)-6,7-didehydro-4,5α-epoxy-3-hydroxypyrido[2',3':6,7]morphinan, 5'-(4-Chlorophenyl)-17-(cyclopropylmethyl)-6,7-didehydro-4,5α-epoxy-3-hydroxy-14-(3-phenylacetoxy)pyrido[2',3':6,7]morphinan, 5'-(4-Chlorophenyl)-17-(cyclopropylmethyl)-6,7-didehydro-4,5α-epoxy-3-hydroxy-14-(3-phenylpropionyloxy)pyrido[2',3':6,7]morphinan, 14-Benzoyloxy-5'-(4-chlorophenyl)-6,7-didehydro-4,5α-epoxy-3-hydroxy-17-methylpyrido[2',3':6,7]morphinan, 5'-(4-Chlorophenyl)-6,7-didehydro-4,5α-epoxy-3-hydroxy-17-methyl-14-(phenylacetoxy)pyrido[2',3':6,7]morphinan, 5'-(4-Chlorophenyl)-6,7-didehydro-4,5α-epoxy-3-hydroxy-17-methyl-14-(3-phenylpropionyloxy)pyrido[2',3':6,7]morphinan, 3,14-Dibenzoyloxy-5'-(4-chlorophenyl)-17-(cyclopropyl-methyl)-6,7-didehydro-4,5α-epoxy-3-hydroxypyrido[2',3':6,7]morphinan, 3-Benzoyloxy-5'-(4-chlorophenyl)-17-(cyclopropylmethyl)-6,7,8,14-tetradehydro-4,5α-epoxypyrido[2',3':6,7]morphinan, and 5'-(4-Chlorophenyl)-17-(cyclopropylmethyl)-3-hydroxy-6,7,8,14-tetradehydro-4,5α-epoxypyrido[2',3':6,7]morphinan, pharmaceutically acceptable salt thereof deuterium forms thereof, isomers thereof, and mixture thereof.

4. A pharmaceutical composition comprising a compound according to claim 1, pharmaceutically acceptable salts thereof, deuterated forms thereof isomers thereof, and mixtures thereof and a pharmaceutically acceptable carrier.

5. A method for treating a patient suffering from pain which comprises administering to the patient a pain treating effective amount of at least one compound according to claim 1, pharmaceutically salt thereof, deuterium forms thereof, isomers thereof, and mixture thereof.

6. A process for the preparation of a compound of the formula according to claim 1 which comprises subjecting a 17-substituted-3,14-dihydroxypyridomorphinan to dialkylation at the phenolic hydroxyl at the 3-position and the tertiary alcohol at the 14-position followed by selective dealkylation of the phenolic ether function.

7. A pharmaceutical composition comprising a compound according to claim 2, pharmaceutically acceptable salts thereof, deuterated forms thereof, isomers thereof, and mixtures thereof and a pharmaceutically acceptable carrier.

8. A pharmaceutical composition comprising a compound according to claim 3, pharmaceutically acceptable salts thereof, deuterated forms thereof, isomers thereof, and mixtures thereof and a pharmaceutically acceptable carrier.

9. A method for treating a patient suffering from pain which comprises administering to the patient a pain treating effective amount of at least one compound according to claim 2, pharmaceutically salt thereof, deuterium forms thereof, isomers thereof, and mixture thereof.

10. A method for treating a patient suffering from pain which comprises administering to the patient a pain treating effective amount of at least one compound according to claim 3, pharmaceutically salt thereof, deuterium forms thereof, isomers thereof, and mixture thereof.

11. A process for the preparation of a compound of the formula according to claim 2 which comprises subjecting a 17-substituted-3,14-dihydroxypyridomorphinan to dialkylation at the phenolic hydroxyl at the 3-position and the tertiary alcohol at the 14-position followed by selective dealkylation of the phenolic ether function.

12. A process for the preparation of a compound of the formula according to claim 3 which comprises subjecting a 17-substituted-3,14-dihydroxypyridomorphinan to dialkylation at the phenolic hydroxyl at the 3-position and the tertiary alcohol at the 14-position followed by selective dealkylation of the phenolic ether function.

13. The compound of claim 1, wherein A is O.

14. A method for treating a patient suffering from pain which comprises administering to the patient a pain treating effective amount of at least one compound or composition according to claim 13, pharmaceutically salt thereof, deuterium forms thereof, isomers thereof, and mixture thereof.

15. The compound of claim 1, wherein $R_5$ is selected from the group consisting of substituted or unsubstituted aryl or heteroaryl.

16. A method for treating a patient suffering from pain which comprises administering to the patient a pain treating effective amount of at least one compound or composition according to claim 15, pharmaceutically salt thereof, deuterium forms thereof, isomers thereof, and mixture thereof.

* * * * *